US010266855B2

(12) United States Patent
Kawata et al.

(10) Patent No.: US 10,266,855 B2
(45) Date of Patent: Apr. 23, 2019

(54) **METHOD FOR MANUFACTURING 3-HYDROXYBUTYRIC ACID USING *HALOMONAS* SP**

(71) Applicants: NATIONAL INSTITUTE OF ADVANCED INDUSTRIAL SCIENCE AND TECHNOLOGY, Tokyo (JP); OSAKA GAS CO., LTD., Osaka-shi, Osaka (JP)

(72) Inventors: Yoshikazu Kawata, Ikeda (JP); Jun Tsubota, Osaka (JP); Isao Matsushita, Osaka (JP)

(73) Assignees: NATIONAL INSTITUTE OF ADVANCED INDUSTRIAL SCIENCE AND TECHNOLOGY, Tokyo (JP); OSAKA GAS CO., LTD., Osaka (JP)

( * ) Notice: Subject to any disclaimer, the term of this patent is extended or adjusted under 35 U.S.C. 154(b) by 0 days.

(21) Appl. No.: 15/035,949

(22) PCT Filed: Nov. 11, 2014

(86) PCT No.: PCT/JP2014/079855
§ 371 (c)(1),
(2) Date: May 11, 2016

(87) PCT Pub. No.: WO2015/072456
PCT Pub. Date: May 21, 2015

(65) Prior Publication Data
US 2016/0265007 A1 Sep. 15, 2016

(30) Foreign Application Priority Data

Nov. 12, 2013 (JP) .................. 2013-233961
Feb. 20, 2014 (JP) .................. 2014-030915
May 21, 2014 (JP) .................. 2014-105522

(51) Int. Cl.
*C12N 1/20* (2006.01)
*C12P 7/42* (2006.01)

(52) U.S. Cl.
CPC . *C12P 7/42* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 5,461,073 A | 10/1995 | Katayama | |
| 6,472,188 B1 | 10/2002 | Lee et al. | |
| 9,273,331 B2 | 3/2016 | Kawata | |
| 2011/0270865 A1 | 11/2011 | Oookuma | |
| 2014/0363863 A1 | 12/2014 | Kawata | |

FOREIGN PATENT DOCUMENTS

| | | |
|---|---|---|
| CN | 102120973 A | 7/2011 |
| EP | 2767590 A1 | 8/2014 |
| JP | H07-061924 A | 3/1995 |
| JP | 3579352 B2 | 10/2004 |
| JP | 2005-306815 A | 11/2005 |
| JP | 2010-168595 A | 8/2010 |
| JP | 2010-273582 A | 12/2010 |
| JP | 2013-081403 A | 5/2013 |
| JP | 2016-202093 A | 12/2016 |
| WO | WO 1999/029889 A1 | 6/1999 |
| WO | WO 2009/041531 A1 | 4/2009 |
| WO | WO 2013/051499 A1 | 4/2013 |

OTHER PUBLICATIONS

Kawata et al., Appl. Microbiol Biotechnol, 2012, vol. 96, p. 913-920.*
Tan et al., Bioresource Technology, 2011, vol. 102, p. 8130-8136.*
Quillaguaman et al., Appl. Microbiol. Biotechnol. , 2007, vol. 74, p. 981-986.*
Quillaguaman et al., Journal of Applied Microbiology, 2005, vol. 99, p. 151-157.*
Liu et al., *Appl. Microbiol. Biotechnol.*, 76: 811-818 (2007).
Mabinya et al., *Molecules*, 16: 4358-4370 (2011).
Monteil-Rivera et al., *Journal of Chromatography A*, 1154: 34-41 (2007).
Ugwu et al., *Bioresource Technology*, 102(12): 6766-6768 (2011).
Japanese Patent Office, International Search Report in International Application No. PCT/JP2014/079855 (dated Feb. 3, 2015).
Jin et al., *Bioresource Technology*, 140: 73-79 (2013).
Kawata et al., *Bioresource Technology*, 140: 443-445 (2013).
Kawata et al., *Bioresource Technology*, 156: 400-403 (2014).
Wu et al., *Int. J. Syst. Evol. Microbiol.*, 58: 2859-2865 (2008).
Zhao et al., *Int. J. Syst. Evol. Microbiol.*, 62(Pt 1): 173-178 (2012).
European Patent Office, Supplementary European Search Report in European Patent Application No. 14862581.7 (dated Jun. 8, 2017).
Japanese Patent Office, Notification of Reasons for Refusal in Japanese Patent Application No. 2014-187957 (dated Jun. 13, 2017).
Tokiwa et al., "Chemical synthesis and biodegradation of copolymers using (R)-3-hydroxybutyric acid derived from microbial polyhydroxybutyrate," *The 65th Annual Meeting of the Society for Biotechnology Japan*, 65: 72, Abstract 1P-219 (2013).
Yokaryo et al., "(R)-3-hydroxybutyric acid production from molasses by alkaliphilic bacteria isolated from Okinawa," *Annual Meeting of the Society for Biotechnology Japan*, 65: 72, Abstract 1P-220 (2013).

(Continued)

*Primary Examiner* — Kade Ariani

(74) *Attorney, Agent, or Firm* — Leydig, Voit & Mayer, Ltd.

(57) ABSTRACT

The invention provides a process for producing 3-hydroxybutyric acid or a salt thereof, the process comprising culturing one or more halophilic bacteria belonging to the genus *Halomonas* under specific conditions.

21 Claims, 16 Drawing Sheets

(56) References Cited

OTHER PUBLICATIONS

Japanese Patent Office, Notification of Reasons for Refusal in Japanese Patent Application No. 2014-187957 (dated Oct. 3, 2017).
D'Alessio et al., "Transcriptome Analysis of Polyhydroxybutyrate Cycle Mutants Reveals Discrete Loci Connecting Nitrogen Utilization and Carbon Storage in *Sinorhizobium meliloti*," *mSystems*, 2(5): e00035-17 (2017).
Hannya et al., "Efficient production and secretion of oxaloacetate from *Halomonas* sp. KM-1 under aerobic conditions," *AMB Express*, 7(1): 209 (2017).
Kawata et al., "Poly(3-hydroxybutyrate) Production by Isolated *Halomonas* sp. KM-1 Using Waste Glycerol," *Biosci. Biotechnol. Biochem.*, 74(1): 175-177 (2010).

\* cited by examiner

METHOD FOR MANUFACTURING 3-HYDROXYBUTYRIC ACID USING *HALOMONAS* SP

CROSS-REFERENCE TO RELATED APPLICATIONS

This patent application is the U.S. national phase of International Patent Application No. PCT/JP2014/079855, filed Nov. 11, 2014, which claims the benefit of Japanese Patent Application No. 2013-233961, filed on Nov. 12, 2013, Japanese Patent Application No. 2014-030915, filed on Feb. 20, 2014, and Japanese Patent Application No. 2014-105522, filed on May 21, 2014, which are incorporated by reference in their entireties herein.

TECHNICAL FIELD

The present invention relates to a process for producing 3-hydroxybutyric acid using *Halomonas* bacteria.

BACKGROUND ART

The shift to bio-based material technologies for not only energy but also chemical refineries, and the conversion of industrial starting materials from petroleum to biomass, have become issues in recent years.

In humans, 3-hydroxybutyric acid (hereinafter also referred to as "3-HB" in the present specification), which is produced from acetyl CoA in the liver, is used as an energy source for the brain when blood glucose levels are low. Further, it can prevent the transfer of enterobacteria into the blood. Therefore, the use of 3-hydroxybutyric acid in infusions, eye-drops, etc., and its use as a starting material for biodegradable plastics have been examined (PTL 1 and PTL 2).

Known processes for producing 3-hydroxybutyric acid are as follows. For example, since this compound is a monomer of poly-3-hydroxybutyrate (hereinafter also referred to as "PHB" in the present specification), PHB is produced by various bacterial cells, and then degraded by lipases, etc., which have been prepared separately, to thereby obtain 3-hydroxybutyric acid, which is a monomer of PHB (PTL 3). NPL 1 shows a process in which 8.7 g/L of 3-hydroxybutyric acid is obtained by using mutants, and NPL 2 shows a process in which 3-hydroxybutyric acid is obtained with a yield of 12 g/L by using a gene recombination technique.

The present inventors examined an efficient process of culturing *Spirulina* microalgae, and found that a specific basophilic bacterium grew under certain conditions as the only contaminating bacterium. Since the halophilic bacteria generally grew well in a medium with a pH of about 5 to 12 containing a high concentration of sodium, it was presumed that contamination by other bacteria hardly occurred, even under aerobic fermentation. Then, examination of the assimilation of various carbon sources by the halophilic bacteria revealed that a remarkable amount of PHB was accumulated in the cells of the halophilic bacteria (PTL 4).

In the course of subsequent studies, it was found that halophilic bacteria belonging to the genus *Halomonas* accumulated PHB under aerobic conditions, and that when the aerobic conditions were shifted to microaerobic conditions, 3-hydroxybutyric acid, which is a monomer of PHB, was secreted and produced in the culture medium (PTL 5).

It is known that 3-hydroxybutyric acid is contained in a remarkable amount in breast milk, and is derived from fatty acid, etc., at a low glucose concentration. It is also known that the metabolic speed of 3-hydroxybutyric acid is relatively fast. Methyl esters of 3-hydroxybutyric acid are expected to be useful as health foods, etc., and particularly supplements suitable for athletes.

Thus, 3-hydroxybutyric acid is a very useful starting chemical material as original acidic form mentioned above, or as a polymer comprising 3-hydroxybutyric acid as a constituent unit.

CITATION LIST

Patent Literature

PTL 1: JPH07-61924A
PTL 2: JP2005-306815A
PTL 3: JP2010-168595A
PTL 4: WO2009/041531
PTL 5: JP2013-081403A.

Non-Patent Literature

NPL 1: Bioresource Technology, Volume 102, Issue 12, June 2011, pp, 6766-6768, Charles U. Ugwu, Yutaka Tokiwa, and Toshio Ichiba NPL 2: Appl Microbiol Biotechnol (2007) 76:811-818 Qian Liu, Shao-Ping Ouyang, Ahleum Chung, Qiong Wu, and Guo-Qiang Chen NPL 3: J. Chromatogr. A, Jun. 22, 2007; 1154(1-2): 34-41, Monteil-Rivera F et al.

SUMMARY OF INVENTION

Technical Problem

PTL 5, which discloses an invention characterized by changing the culture conditions from aerobic conditions to microaerobic conditions, discloses a process for producing 3-hydroxybutyric acid or a salt thereof using halophilic bacteria belonging to the genus *Halomonas*, and shows an Example in which 20 g/L of 3-hydroxybutyric acid was secreted and produced in a culture medium when a medium containing 15% glucose was used.

This process is advantageous in that 3-hydroxybutyric acid can be easily collected from the culture medium; however, because the yield is only about 20 g/L, it can hardly be said that this process is industrially sufficient.

Therefore, it is desired that a larger amount of PHB accumulated in the bacterial cells is degraded, and that 3-hydroxybutyric acid or a salt thereof is more efficiently secreted and produced in the culture medium.

Considering the above, an object of the present invention is to provide a process for producing 3-hydroxybutyric acid and a salt thereof using halophilic bacteria belonging to the genus *Halomonas*, wherein PHB accumulated in the bacterial cells is degraded, 3-hydroxybutyric acid is efficiently secreted and produced in a culture medium, and the 3-hydroxybutyric acid is collected from the culture medium.

Solution to Problem

The present inventors conducted extensive research against this background, and found that PHB accumulated in halophilic bacterial cells belonging to the genus *Halomonas* was degraded, and a remarkable amount of 3-hydroxybutyric acid was secreted in the culture medium by adding an organic carbon source as well as nitrogen, a metal salt, borate, etc., to the medium at the stage of making the bacterial cells to accumulate a remarkable amount of PHB therein, performing aerobic culture, then changing the culture conditions to microaerobic conditions, and causing the bacterial cells to degrade a remarkable amount of PHB accumulated therein to secrete and produce 3-hydroxybutyric acid in the culture medium outside of the bacterial cells.

It was also found that the yield of 3-hydroxybutyric acid could be increased by using a specific nitrogen source.

Further, it was also found that a higher concentration of 3-hydroxybutyric acid could be secreted and produced by adding a nitrogen source, a metal salt, borate, etc., before mioroaerobic culture, reducing the volume of the culture medium, and adjusting and/or maintaining the pH within a specific range.

The present invention has been completed based on these findings, and includes inventions according to a wide range of embodiments shown below.

[Item 1]
A process for producing 3-hydroxybutyric acid or a salt thereof, the process comprising the following steps (1) to (3):
(1) step 1 of culturing one or more halophilic bacteria belonging to the genus *Halomonas* under aerobic conditions in a medium containing an organic carbon source and an inorganic salt;
(2) step 2 of changing the culture conditions in step 1 from aerobic culture to microaerobic culture, and culturing bacterial cells of the halophilic bacteria to produce 3-hydroxybutyric acid or a salt thereof in a culture medium; and
(3) step 3 of collecting the 3-hydroxybutyric acid or the salt thereof from the culture medium obtained in step 2.

[Item 2]
The production process according to item 1, wherein the inorganic salt comprises urea.

[Item 3]
The production process according to item 1 or 2, wherein the culture conditions are changed from aerobic culture to microaerobic culture in step 2 when the amount of PHB accumulated in the bacterial cells is 70 parts by weight or more per 100 parts by weight of dry cells.

[Item 4]
The production process according to any one of items 1 to 3, wherein before step 2, the process comprises a step of adding at least one member selected from the group consisting of nitrogen sources, metal salts, and borate to the culture medium.

[Item 5]
The production process according to item 4, wherein the nitrogen source is at least one member selected from the group consisting of nitrate, nitrite, ammonium salts, and urea.

[Item 6]
The production process according to item 4 or 5, wherein the metal salt is at least one member selected from the group consisting of zinc salts, molybdenum salts, manganese salts, copper salts, and cobalt salts.

[Item 7]
The production process according to any one of items 4 to 6, wherein at least one member selected from the group consisting of nitrogen sources, metal salts, and borate is added to the culture medium when the amount of PHB accumulated in the bacterial cells is 70 parts by weight or more per 100 parts by weight of dry cells.

[Item 8]
The production process according to any one of items 1 to 7, wherein before step 2, the process comprises a step of reducing the volume of the culture medium.

[Item 3]
The production process according to any one of items 1 to 8, wherein after step 2, the process comprises a step of adjusting and/or maintaining the pH of the culture medium at 7 or more.

[Item 10]
The production process according to item 9, wherein the pH of the culture medium is adjusted and/or maintained at 7.5 or more.

[Item 11]
The production process according to item 9 or 10, wherein the pH of the culture medium is adjusted and/or maintained using at least one member selected from the group consisting of hydroxide, carbonate, and hydrogen carbonate.

[Item 12]
The production process according to any one of items 1 to 11, wherein the halophilic bacteria; comprise *Halomonas* sp. KM-1 strain (FERM BP-10995).

Advantageous Effects of Invention

According to the production process of the present invention, a remarkable amount of 3-hydroxybutyric acid or a salt thereof can be produced in a medium.

The production process of the present invention includes the step of culturing halophilic bacteria belonging to the genus *Halomonas*. The halophilic bacteria can be cultured in an environment where contamination by other bacteria hardly occurs, the culture can be performed in a non-sterilized medium and/or a non-sterilized environment, and the air supply conditions can be easily changed. Therefore, the production process of the present invention is excellent.

The halophilic bacteria used in the production process of the present invention can use, for example, inexpensive inorganic salts, as well as waste glycerol produced as a by-product in the production of biodiesel, wood saccharification liquid produced in the process of ethanol fermentation, and organic acids obtained by fermentation of food scraps, etc., as organic carbon sources singly or in combination with other organic carbon sources. Further, pentoses, such as xylose and arabinose, which are obtained by ethanol fermentation using yeast cells and are difficult to use, can also be effectively used as organic carbon sources.

The production process of the present invention can produce 3-hydroxybutyric acid or a salt thereof in the culture medium. Thus, fractions containing the 3-hydroxybutyric acid or the salt thereof can be easily collected from the culture medium. Even when purification is performed, a simple purification method can be applied. Therefore, the production process of the present invention is excellent.

In this regard, because the 3-hydroxybutyric acid or the salt thereof can be collected from the culture medium, of the basophilic bacterial ceils belonging to the genus *Halomonas* under conditions that do not cause bacteriolysis of the cells, the production process of the present invention has the effect of purifying the 3-hydroxybutyric acid or the salt thereof by a very simple purification method for removing contaminating molecules, such as nucleic acid, protein, sugar, and lipid, resulting from bacteriolysis.

In particular, according to the process of the present invention, the culture medium at the time of collecting 3-hydroxybutyric acid is alkaline. In such an environment, 3-hydroxybutyric acid is less likely to form salts. Therefore, the process of the present invention is effective in collecting 3-hydroxybutyric acid.

The 3-hydroxybutyric acid or the salt thereof obtained by the production process of the present invention can be added to medical infusions, or polymerized as it is to form a plastic material. The 3-hydroxybutyric acid or the salt thereof is also useful as cosmetics, drugs, functional foods, optically active materials, and chemical starting materials.

DESCRIPTION OF EMBODIMENTS

Figure 1:
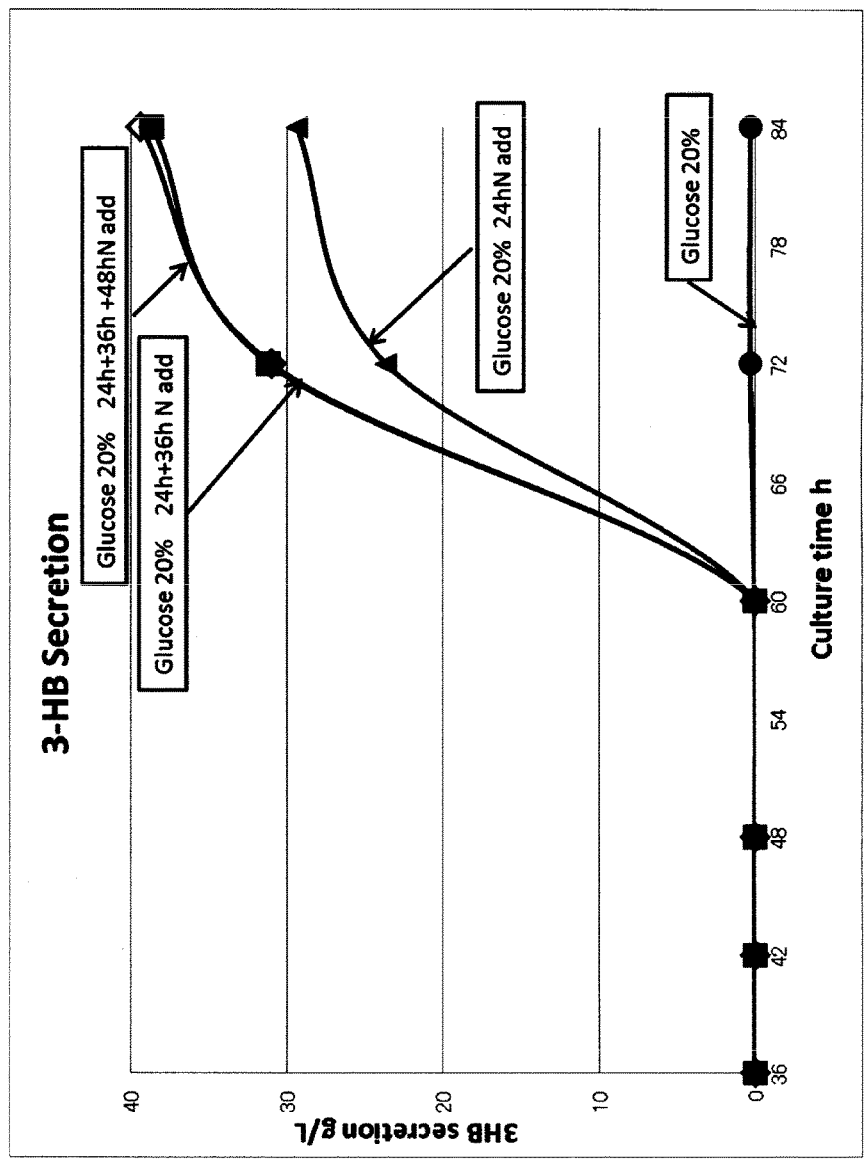
FIG. 1 is a graph showing the ratio of 3-hydroxybutyric acid or a salt thereof accumulated in the culture supernatant (vertical axis: 3-hydroxybutyric acid or a salt thereof (g)/culture supernatant (L), and the culture time (horizontal axis: h)) obtained by the process shown in Production Example 1 in the Examples. Filled circles (●) in the graph show the results when 20% glucose was added to a modified SOT 5 medium. Filled triangles (▲) in the graph show the results when 20% glucose was added to a modified SOT 5 medium, and sodium nitrate as a nitrogen source was further added 24 hours after the start of culture. Filled squares (■) in the graph show the results when 20% glucose was added to a modified SOT 5 medium, and sodium nitrate as a nitrogen source was further added 24 hours and 36 hours after the start of culture. Open diamonds (◇) in the graph show the results when 20% glucose was added to a modified SOT 5 medium, and sodium nitrate as a nitrogen source was further added 24 hours, 36 hours, and 48 hours after the start of culture.
Figure 2:
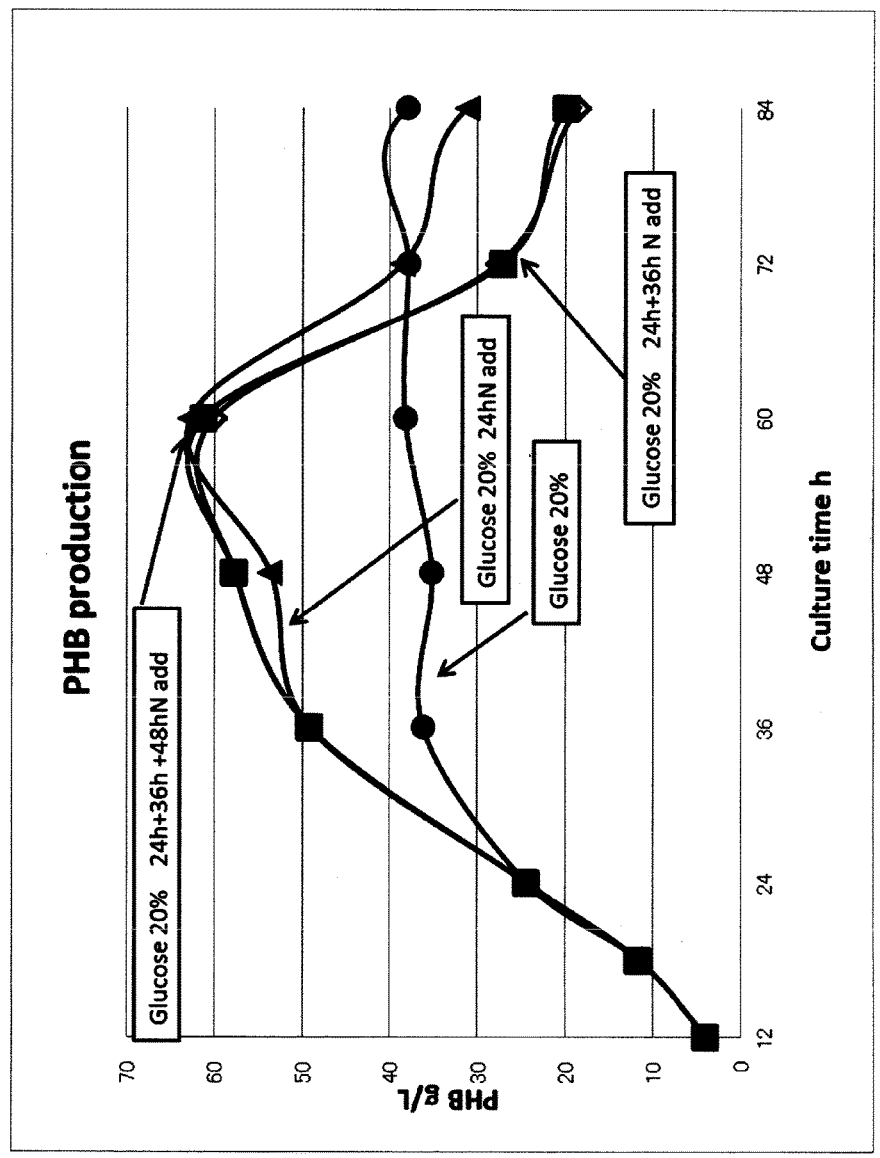
FIG. 2 is a graph showing the amount of PHB (vertical axis: PHB (g)/culture supernatant (L), and the culture time (horizontal axis: h)) obtained by the process shown in Production Example 1 in the Examples. Filled circles (●) in the graph show the results when 20% glucose was added to a modified SOT 5 medium. Filled triangles (▲) in the graph show the results when 20% glucose was added to a modified SOT 5 medium, and sodium nitrate as a nitrogen source was further added 24 hours after the start of culture. Filled squares (■) in the graph show the results when 20% glucose was added to a modified SOT 5 medium, and sodium nitrate as a nitrogen source was further added 24 hours and 36 hours after the start of culture. Open diamonds (◇) in the graph show the results when 20% glucose was added to a modified SOT 5 medium, and sodium nitrate as a nitrogen source was further added 24 hours, 36 hours, and 48 hours after the start of culture.
Figure 3:
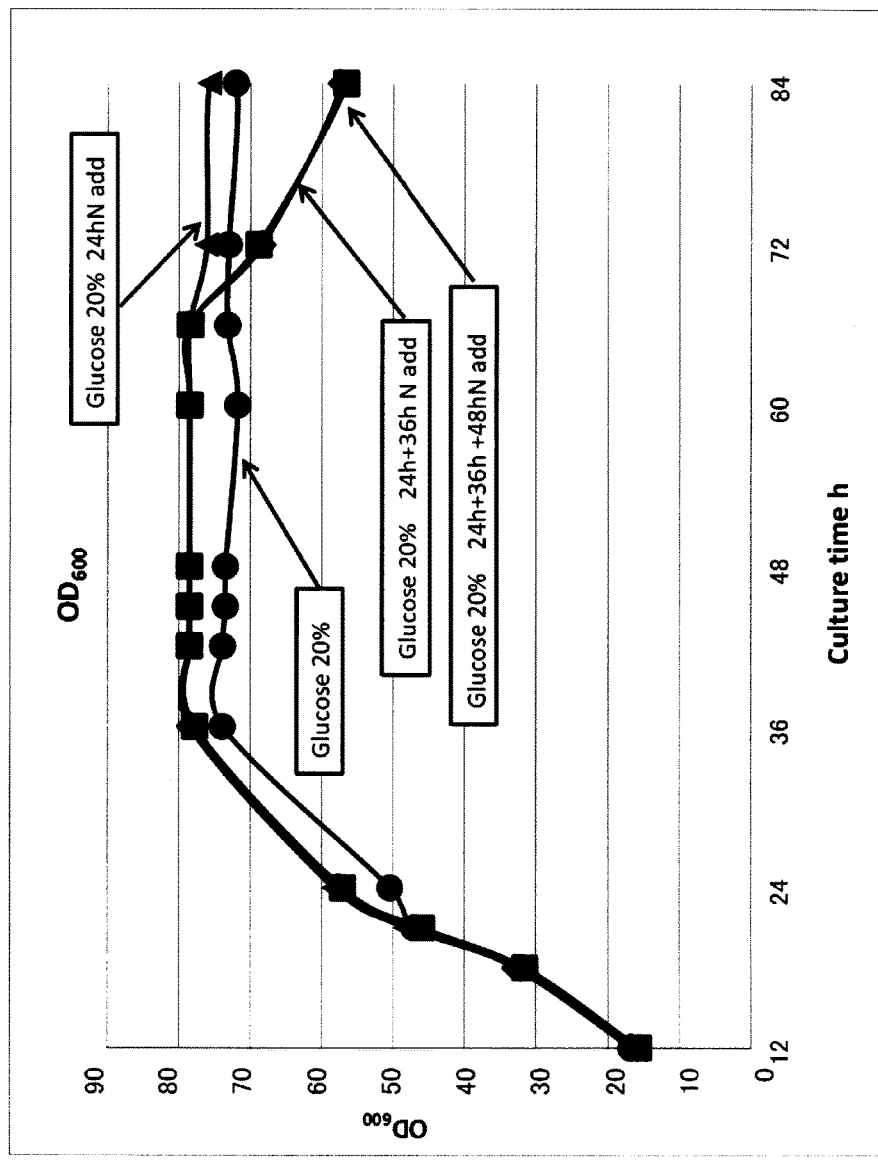
FIG. 3 is a graph showing the amount of bacterial cells (vertical axis: $OD_{600}$, and the culture time (horizontal axis: h)) obtained by the process shown in Production Example 1 in the Examples. Filled circles (●) in the graph show the results when 20% glucose was added to a modified SOT 5 medium. Filled triangles (▲) in the graph show the results; when 20% glucose was added to a modified SOT 5 medium, and sodium nitrate as a nitrogen source was further added 24 hours after the start of culture. Filled squares (■) in the graph show the results when 20% glucose was added to a modified SOT 5 medium, and sodium nitrate as a nitrogen source was further added 24 hours and 36 hours after the start of culture. Open diamonds (◇) in the graph show the results when 20% glucose was added to a modified SOT 5 medium, and sodium nitrate as a nitrogen source was further added 24 hours, 36 hours, and 48 hours after the start of culture.
Figure 4:
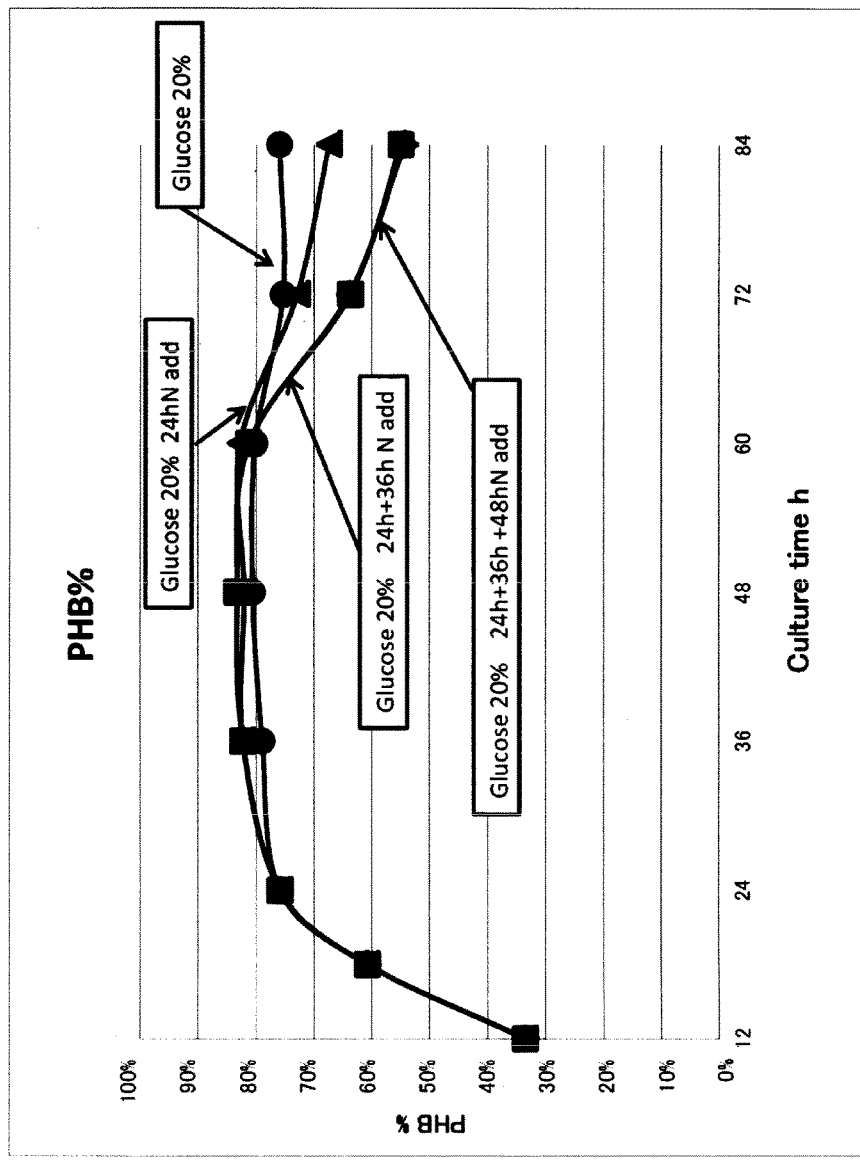
FIG. 4 is a graph showing the amount of PHB accumulated in bacterial cells (vertical axis: PHB (%): PHB (g)/dry cell weight (g), and the culture time (horizontal axis: h)) obtained by the process shown in Production Example 1 in the Examples. Filled circles (●) in the graph show the results when 20% glucose was added to a modified SOT 5 medium. Filled triangles (▲) in the graph show the results when 20% glucose was added to a modified SOT 5 medium, and sodium nitrate as a nitrogen source was further added 24 hours after the start of culture. Filled squares (■) in the graph show the results when 20% glucose was added to a modified SOT 5 medium, and sodium nitrate as a nitrogen source was further added 24 hours and 36 hours after the start of culture. Open diamonds (◇) in the graph show the results when 20% glucose was added, to a modified SOT 5 medium, and sodium nitrate as a nitrogen source was further added 24 hours, 36 hours, and 48 hours after the start of culture.

The process for producing 3-hydroxybutyric acid or a salt thereof according to the present invention comprises the following steps (1) to (3) (this is also referred to as the first embodiment in the present specification):

(1) step 1 of culturing one or more halophilic bacteria belonging to the genus *Halomonas* under aerobic conditions in a medium containing an organic carbon source and an inorganic salt;

(2) 2 of changing the culture conditions in step 1 from aerobic culture to microaerobic culture, and culturing bacterial cells of the halophilic bacteria to produce 3-hydroxybutyric acid or a salt thereof in a culture medium; and (3) step 3 of collecting the 3-hydroxybutyric acid or the salt thereof from the culture medium obtained in step 2.

The 3-hydroxybutyric acid or the salt thereof produced by the production process of the present invention is a compound having ordinary optical activity in the living body, and is a D-isomer.

Salts of 3-hydroxybutyric acid are formed by cations derived from components contained in the medium of the halophilic bacteria belonging to the genus *Halomonas* used in the production, and/or by cations present in the bacterial cells. Examples thereof include, but are not limited to, sodium salts, potassium salts, calcium salts, magnesium salts, cobalt salts, zinc salts, iron salts, copper salts, molybdenum salts, ammonium salts, lithium salts, silver salts, mercury salts, strontium salts, barium salts, cadmium salts, nickel salts, tin salts, lead salts, manganese salts, aluminum salts, and the like.

Step 1

Step 1 of the production process of the present invention is a step of culturing halophilic bacteria belonging to the genus *Halomonas* under aerobic conditions in a medium containing an organic carbon source and an inorganic salt.

A: Halophilic Bacteria

The halophilic bacteria used in step 1 of the production process of the present invention may be those belonging to the genus *Halomonas* shown in (i) or (ii) below:

(i) Halophilic bacteria that grow aerobically in a medium containing an inorganic salt and one or more organic carbon sources, and that produce 3-hydroxybutyric acid or a salt thereof in a medium outside of the bacterial cells; or (ii) Halophilic bacteria that grow aerobically in a medium containing an inorganic salt and one or more organic carbon sources, and that accumulate PHB in their own bacterial cells and then secrete and produce 3-hydroxybutyric acid or a salt thereof in a culture medium outside of the bacterial cells under microaerobic conditions.

The inorganic salt and organic carbon source will be described later in the "Medium" section; however, the inorganic salt preferably comprises urea. The microaerobic conditions will be described in detail below in the "Culture Condition" section in step 2.

Such halophilic bacteria belonging to the genus *Halomonas* can undergo both oxidative metabolism and anaerobic metabolism, and can survive regardless of the presence of free oxygen. They also have the properties of the "facultative anaerobes," which tend to grow better in the presence of free oxygen.

The halophilic bacteria belonging to the genus *Halomonas* have halophilic properties that prefer a salt concentration of 0.1 to 1.0 M, and they can occasionally grow in a salt-free medium. The halophilic bacteria belonging to the genus *Halomonas* generally grow in a medium with a pH of about 5 to 12.

The halophilic bacteria belonging to the genus *Halomonas* are, for example, *Halomonas* sp. KM-1 strain. The *Halomonas* sp. KM-1 strain was deposited with the National institute of Advanced Industrial Science and Technology International Patent Organism Depositary (Chuo-6. Higashi 1-1-1, Tsukuba-shi, Ibaraki, 305-8566, Japan) under the accession number FERM P-21316 dated Jul. 10, 2007, and has been internationally deposited under the accession number FERM BP-10995. The 16S rRNA gene of *Halomonas* sp. KM-1 strain has been registered in DDBJ under the accession number AB477015.

Moreover, in view of the above growth characteristics of the halophilic bacteria belonging to the genus *Halomonas*, *Halomonas pantelleriensis* (ATCC 700273), *Halomonas campisalis* (ATCC 700597), and other halophilic bacteria can also be used in the production process of the present invention, in addition to the *Halomonas* sp. KM-1 strain.

Furthermore, 16S ribosomal RNA sequence analysis shows that not only can the above halophilic bacteria belonging to the genus *Halomonas*, but also *Halomonas nitritophilus*, *Halomonas alimentaria*, etc., be used as the halophilic bacteria belonging to the genus *Halomonas* used in the production process of the present invention.

Genes may be introduced into the halophilic bacteria belonging to the genus *Halomonas*. Genes to be introduced are not particularly limited, as long as they can develop the function of improving the production efficiency, etc., of 3-hydroxybutyric acid or a salt thereof in the production process of the present invention. Examples thereof include genes that increase PHB expression levels, genes that develop the function of increasing PHB accumulation in the bacterial cells, genes that promote the function of producing 3-hydroxybutyric acid or a salt thereof in the culture medium, genes that increase the amount of 3-hydroxybutyric acid or a salt thereof produced, genes that degrade PHB, and the like. As the method of introducing a recombinant DNA to the bacterial cells, and the method of transformation with the recombinant DNA, various general methods can be used.

B: Medium

The medium used in step 1 contains an inorganic salt and an organic carbon source. Although the pH of the medium is not particularly limited, the pH preferably satisfies the above growth conditions of the halophilic bacteria. Specifically, the pH is preferably about 5 to 12, and more preferably 8.8 to 12. The use of an alkaline medium is preferred because contamination by other bacteria can be prevented more effectively, and because the conversion of secreted 3-hydroxybutyric acid to crotonic acid can be prevented.

The inorganic salt added to the medium used in step 1 is not particularly limited. Examples thereof include phosphate, nitrate, carbonate, and sulfate; and metal salts of sodium, magnesium, potassium, manganese, iron, zinc, copper, cobalt, etc.

For example, when sodium is used as the inorganic salt, it is possible to use NaCl, $NaNO_3$, $NaHCO_3$, $Na_2CO_3$, or the like.

As these inorganic salts, it is preferable to use compounds that can serve as nitrogen sources or phosphorus sources for the halophilic bacteria.

Examples of nitrogen sources include nitrate, nitrite, ammonium salts, urea, etc. Specific examples include, but are not limited to, $NaNO_3$, $NaNO_2$, $NH_4Cl$, urea, and other compounds. Among these, urea is particularly preferred.

The inorganic salt contained in the medium used in step 1 preferably comprises urea.

The amount of nitrogen source used may be suitably determined within a range that does not affect the growth of the bacterial cells and that can achieve the purpose of the present invention, to produce 3-hydroxybutyric acid or a salt thereof. Specifically, the amount of nitrate per 100 ml of the medium at the beginning of culture is generally about 500 mg or more, preferably about 1,000 mg or more, and more preferably about 1,250 mg or more.

When urea is used as the nitrogen source, its amount may be 200 mg or more per 100 ml of the medium at the beginning of culture, and more preferably about 400 to 700 mg in which 3-hydroxybutyric acid or a salt thereof can be produced more efficiently.

Examples of phosphorus sources include phosphate, monohydrogen phosphate, dihydrogen phosphate, etc. Specific examples include, but are not limited to, $K_2HPO_4$, $KH_2PO_4$, and other compounds.

The amount of phosphorus source used may also be suitably determined from the same viewpoint as for the amount of nitrogen source mentioned above. Specifically, the amount of dihydrogen phosphate per 100 ml of the medium is generally about 50 to 400 mg, and preferably about 100 to 200 mg.

These inorganic salts may be used singly or in combination of two or more.

The total concentration of inorganic salt, including other compounds, etc., is generally about 0.1 to 2.5 M, preferably about 0.2 to 1.0 M, and more preferably about 0.2 to 0.5 M.

The organic carbon source added to the medium used in step 1 is not particularly limited. Examples thereof include tryptone, yeast extract, soluble starch, ethanol, n-propanol, acetic acid, sodium acetate, propionic acid, waste glycerol, exhausted molasses, wood saccharification liquid; hexoses, such as psicose, fructose, sorbose, tagatose, allose, altrose, glucose, mannose, gulose, idose, galactose, and talose; pentoses, such as ribulose, xylulose, ribose, arabinose, xylose, lyxose, and deoxyribose; disaccharides, such as sucrose, lactose, maltose, trehalose, turanose, and cellobiose; sugar alcohols, such as erythritol, glycerol, mannitol, sorbitol, and xylitol; and the like.

According to the production process of the present invention, the halophilic bacteria belonging to the genus *Halomonas* are cultured in a medium with a relatively high salt concentration, and this causes little risk of contamination by other bacterial cells and growth of such bacterial cells. Therefore, the above median may be or may not be subjected to sterilization or other treatment, and culture by using simple equipment is possible.

C: Culture Condition

Aerobic culture is used to culture the halophilic bacteria belonging to the genus *Halomonas* in step 1. The aerobic culture in step 1 is not particularly limited, as long as it enables the bacterial cells to grow and to accumulate a large amount of PHB therein.

Specifically, the halophilic bacteria are seeded in about 5 ml of medium, and pre-cultured with shaking generally at about 30 to 37° C. and at a stirring rate of about 120 to 180 rpm overnight. The pre-cultured cells are then diluted about 100 times in a medium that is placed in an Erlenmeyer flask, fermenter, jar fermenter, or the like, for main culture.

The main culture is preferably carried out at about 30 to 37° C., although it is generally possible to carry out the main culture at 20 to 45° C. The stirring rate in this case is generally about 150 to 250 rpm. The culture environment may be such that the medium is exposed to the air. A gas containing oxygen may be actively sprayed to the surface of the culture medium, or the gas may be blown into the medium.

In step 1, the halophilic bacteria belonging to the genus *Halomonas* may be aerobically cultured under such culture conditions. Specifically, the dissolved oxygen concentration of the culture medium during aerobic culture is generally 2 mg/L or more, and preferably 5 mg/L or more, but is not particularly limited thereto.

Examples of the culture condition in step 1 include, but are not limited to, batch culture, fed-batch culture, continuous culture, and the like. Long-term continuous culture is also possible for efficient production of 3-hydroxybutyric acid or a salt thereof, in view of the very low risk of contamination of the halophilic bacteria used in the process of the present invention by other bacteria. The culture environment is also not particularly limited, and may be a non-sterilized environment or a sterilized environment.

Step 2

Step 2 of the production process of the present invention is a step of changing the culture conditions in step 1 from aerobic culture to microaerobic culture, and culturing the bacterial cells to produce 3-hydroxybutyric acid or a salt thereof in the culture medium.

In step 2, when the culture conditions are changed to microaerobic conditions, after the halophilic bacteria belonging to the genus *Halomonas* cultured in step 1 are collected, they may be cultured in a new medium under microaerobic conditions, cultured in the same medium while the culture conditions are changed to microaerobic conditions, or cultured with the addition of a new medium to the culture medium obtained in step 1.

The time to end the aerobic culture in step 1 and change the culture conditions to microaerobic conditions in step 2 is preferably set to the time when the amount of PHB accumulated in the halophilic bacterial cells belonging to the genus *Halomonas* obtained in steps 1 and 2 reaches the maximum value.

The time of the maximum value is not necessarily limited to one time point. Specifically, the culture conditions may be changed to microaerobic conditions, for example, when the amount of PHB accumulated in the halophilic bacterial cells belonging to the genus *Halomonas* obtained in step 1 is about 30 g or more per liter of the culture medium, or when the amount of PHB accumulated in the bacterial cells is about 70 parts by weight or more per 100 parts by weight of dry cells.

The specific amount of PHB accumulated in the halophilic bacterial ceils belonging to the genus *Halomonas* is measured by using the method shown in the Examples, described later.

D: Culture Condition

The microaerobic culture in step 2 indicates culture without positive oxygen ventilation, rather than culture in a medium or culture environment under completely anaerobic conditions.

The culture method under such microaerobic conditions is not particularly limited. For example, the culture is carried out at a stirring rate of 100 rpm or less, preferably 50 rpm or less, while the medium surface is exposed to the air. It is not preferable to completely stop stirring in step 2, because the supply of dissolved oxygen quickly consumed is stopped.

The dissolved oxygen concentration of the culture medium during microaerobic culture is not particularly limited, but is generally 2 mg/L or less. In this case, conditions in which oxygen dissolved in the culture medium is completely absent and oxygen is not supplied are not preferable in step 2, because the halophilic bacteria belonging to the genus *Halomonas* immediately develop bacteriolysis.

In step 2, the halophilic bacteria belonging to the genus *Halomonas*, which accumulate a remarkable amount or PHB in their bacterial cells, obtained in step 1 can be cultured under microaerobic conditions, thereby allowing the culture of the halophilic bacteria without death.

The death of the halophilic bacteria can be confirmed by the presence of DNA eluted from the bacterial cells into the culture medium resulting from the death of the bacterial cells. For example, the extinction can be confirmed by subjecting the culture supernatant of the halophilic bacteria to measurement by using a spectrophotometer to show that no significant absorbance peak based on DNA is present at around 260 nm.

More specifically, in step 2, the halophilic bacteria belonging to the genus *Halomonas* may be cultured under conditions that cause the DNA amount in the culture medium to be within the above range. Such culture conditions that cause the above DNA amount in the culture medium can provide one indication of the fulfillment of the microaerobic conditions in the present invention.

Although the culture time in step 2 varies depending on use conditions, such as the inorganic salt, organic carbon source, etc., used in the medium, it may be a period of time sufficient for collecting the desired amount of 3-hydroxybutyric acid or a salt, thereof, as described later, and is not particularly limited. The culture time may be suitably determined in consideration of simplifying the purification process to remove nucleic acid, protein, etc., released from the halophilic bacteria belonging to the genus *Halomonas* into the culture medium due to bacteriolysis, after the culture condition is changed to microaerobic culture, as described above; that is, the DNA concentration of the culture medium, the concentration of 3-hydroxybutyric acid or salt thereof in the culture medium, and the like.

When the culture conditions are changed to microaerobic conditions in step 2, the pH of the culture medium is generally changed from about 8.7 to about 7.5, and the pH tends to further decrease.

"Producing 3-hydroxybutyric acid in the culture medium" means that the halophilic bacteria belonging to the genus *Halomonas* obtained by culturing in the previous step secrete 3-hydroxybutyric acid into the culture medium from their cells. This step is provided before the final step (collecting step) in the process for producing 3-hydroxybutyric acid or a salt thereof according to the present invention.
Step 3

Step 3 in the production process of the present invention is a step of collecting the 3-hydroxybutyric acid or the salt thereof from the culture medium obtained in step 2.

The term "collecting" as used herein means that after the culture in step 2 is stopped when 3-hydroxybutyric acid or a salt thereof is present in the culture medium obtained in step 2, the culture medium containing the 3-hydroxybutyric acid or the salt thereof is separated from the halophilic bacterial cells.

Specific separation techniques include known solid-liquid separation operations, such as centrifugation and filtration. Moreover, the method of stopping the culture is not particularly limited. For example, the halophilic bacteria belonging to the genus *Halomonas* obtained by steps 1 to 3 are sterilized by heating, acid treatment, or the like; or the culture medium and the halophilic bacterial cells are separated by a known solid-liquid separation method, such as centrifugation or filtration.

When the culture is continued while the 3-hydroxybutyric acid or the salt thereof is contained in the culture medium, particularly when the culture conditions are more aerobic, the halophilic bacteria belonging to the genus *Halomonas* tend to reuptake and use the 3-hydroxybutyric acid or the salt thereof secreted from the halophilic bacterial cells into the culture medium. Consequently, the 3-hydroxybutyric acid or the salt thereof in the culture medium decreases, and finally disappears from the culture medium.

Accordingly, it is preferable to stop the culture when the 3-hydroxybutyric acid or the salt thereof is present in the culture medium in an amount of 40 g or more per liter of the culture medium. That is, according to the process of the present invention, 3-hydroxybutyric acid or salt can be produced in the above culture medium in an amount of about 20 g per liter of the culture medium.

The method of confirming the presence of 3-hydroxybutyric acid or salt thereof in the culture medium, which may vary depending on the type of strain, medium components, culture conditions, and other factors, is suitably determined in consideration of these factors. For example, the time to stop the culture can be determined by continuously sampling the culture medium and subjecting it to an analytical method, such as capillary electrophoresis.

Alternatively, since 3-hydroxybutyric acid is an acidic compound, the presence of 3-hydroxybutyric acid can be confirmed on the basis of decreases in pH of the medium during culture while continuously monitoring the pH of the culture medium.

The salt of 3-hydroxybutyric acid is collected as alkali metal salt reacted with cations of alkali metal or alkaline earth metal, such as sodium or calcium, based on the inorganic salt contained in the culture medium. Accordingly, 3-hydroxybutyric acid can be produced by treating the collected culture medium by salting out or another common method.

The collected culture medium may be subjected to purification by column chromatography using an appropriate column. Alternatively, the pH of the collected culture medium may be suitably changed, and either the desired 3-hydroxybutyric acid or salt thereof may be subjected to purification. Alternatively, a lower alcohol may be added to the collected culture medium to induce an esterification reaction, and the resultant may be purified as 3-hydroxybutyric acid ester by distillation, etc.
Second Embodiment The process for producing 3-hydroxybutyric acid or a salt thereof according to the present invention also includes a second embodiment in which a step of adding at least one member selected from the group consisting of nitrogen sources, metal salts, and borate to the culture medium is added to the above first embodiment.

Examples of this embodiment include a production process comprising the following steps (A) to (D):

(A) step A of culturing one or more halophilic bacteria belonging to the genus *Halomonas* under aerobic conditions in a medium containing an organic carbon source and an inorganic salt;

(B) step B of adding at least one member selected from the group consisting of nitrogen sources, metal salts, and borate to the culture medium of step A;

(C) step C of changing the culture conditions from aerobic culture to microaerobic culture after step B, and culturing bacterial cells of the halophilic bacteria to produce 3-hydroxybutyric acid or a salt thereof in a culture medium; and (D) step D of collecting the 3-hydroxybutyric acid or the salt thereof from the culture medium obtained in step C.

Step A can be the same as step 1 of the first embodiment, step C can be the same as step 2 of the first embodiment, and step D can be the same as step 3 of the first embodiment.

Regarding the step of adding at least one member selected from the group consisting of nitrogen sources, metal salts, and borate to the culture medium (step B), only a nitrogen source may be added, or a metal salt and/or borate may be further added. The time when a nitrogen source is added and the time when a metal salt and/or borate is added may be the same or different, and are not particularly limited. When they are added at different times, it is preferable that a metal salt and/or borate is added after a nitrogen source is added.

The time when a metal salt is added and the time when borate is added may be the same or different, and are not particularly limited.

The nitrogen source may be the same as described in step 1 above.

Examples of metal salts include, but are not particularly limited to, zinc salts, molybdenum salts, manganese salts, copper salts, cobalt salts, and the like. These metal salts may be suitably added in combination. Although it is not particularly limited, a combination including at least a molybdenum salt is preferred.

Specific examples of the combination include metal salts including a molybdenum salt, a zinc salt, a manganese salt, a copper salt, and a cobalt salt; metal salts including a molybdenum salt and a copper salt; metal salts including a molybdenum salt and a zinc salt; metal salts including a molybdenum salt and a manganese salt; metal salts including a molybdenum salt and a cobalt salt; and the like.

Examples of borate include, but are not particularly limited to, boric acid ($H_3BO_3$), metaboric acid ($HBO_2$), perboric acid ($HBO_3$), hypoboric acid ($H_4B_2O_4$), boronic acid ($H_3BO_2$), borinic acid ($H_3BO$), and the like.

The time when at least one member selected from the group consisting of nitrogen sources, metal salts, and borate in step B is added is not particularly limited. For example, the addition may be when the culture medium has an $OD_{600}$ of 50 or more. The $OD_{600}$ is measured by using a commercially available spectrophotometer.

The time when at least one member selected from the group consisting of nitrogen sources, metal salts, and borate is added is not particularly limited. For example, the addition may be when the amount of PHB accumulated in the halophilic bacterial cells belonging to the genus *Halomonas* obtained in step A is 70 parts by weight or more per 100 parts by weight of dry cells, or 25 g or more per liter of the culture medium.

The specific amount of PHB accumulated in the halophilic bacterial cells belonging to the genus *Halomonas* is measured by using the method shown in the following Examples.

The amount of nitrogen source added is not particularly limited, and is generally such that the amount of sodium nitrate is about 0.1 to 0.5 parts by weight based on 100 parts by weight of the medium.

The amount of metal salt added is not particularly limited, and is generally about 0.02 to 0.250 parts by weight based on 100 parts by weight of the medium.

The amount of borate added is not particularly limited, and is generally about 0.143 to 0.286 parts by weight based on 100 parts by weight of the medium.

The total amount of the above metal salt and borate added is generally about 0.02 to 0.286 parts by weight based on 100 parts by weight of the medium.

The number of times at least one member selected from the group consisting of nitrogen sources, metal salts, and borate is added is not particularly limited, and is generally about 1 to 5 times. When the addition is done several times, the addition may be performed at intervals of 3 to 24 hours under the culture conditions describe above.

After at least one member selected from the group consisting of nitrogen sources, metal salts, and borate is added, culture may be carried out under the same culture conditions as those shown in step 1 above for a predetermined period of time before the subsequent step (e.g., step C, described above).

Third Embodiment

The process for producing 3-hydroxybutyric acid or a salt thereof according to the present invention also includes a third embodiment in which a step of adjusting and/or maintaining the pH of the culture medium at 7 or more is added to the first embodiment.

Examples of this embodiment include a production process comprising the following steps (a) to (d):

(a) step a of culturing one or more halophilic bacteria belonging to the genus *Halomonas* under aerobic conditions in a medium containing an organic carbon source and an inorganic salt;

(b) step b of changing the culture conditions from aerobic culture to microaerobic culture after step a;

(c:) step c of adjusting and/or maintaining the pH of the culture medium at 7 or more after step b, and causing the bacterial cells to produce 3-hydroxybutyric acid or a salt thereof in a culture medium; and (d) step d of collecting the 3-hydroxybutyric acid or the salt thereof from the culture medium obtained in step c.

Step a can be the same as step 1 of the first embodiment, step b can be the same as step 2 of the first embodiment, and step d can be the same as step 3 of the first embodiment.

As described in step 2 above, the pH of the medium tends to decrease when the culture conditions are changed from aerobic culture to microaerobic culture. The pH of the culture medium can be suitably confirmed by a known ph-measuring device, a jar fermenter equipped with a ph-measuring device, or the like.

Regarding the step of adjusting and/or maintaining the pH of the culture medium at 7.0 or more (step c), the phrase "adjusting and maintaining" means that while monitoring the pH in the above manner, a pH adjuster is added to maintain the pH within a specific range.

The pH to be adjusted and maintained in step c is preferably 7.5 or more, more preferably 8.0 or more, and even more preferably 8.5 or more. In particular, when the pH is about 8.5 to 9.4, it is expected that about 90% or more of PHB accumulated in the halophilic bacterial cells belonging to the genus *Halomonas* is degraded, and that a remarkable amount of 3-hydroxybutyric acid is secreted in the culture medium.

Since halophilic bacteria belonging to the genus *Halomonas* can generally be cultured at a moderately high salt concentration and under alkaline conditions, there are little incorporation and growth of contaminating bacteria (contamination). However, some lactic acid bacteria can grow even at a moderately high salt concentration and at a pH of 8.4 or less. If the culture system of the present invention is contaminated by such bacteria, the 3-hydroxybutyric acid or the salt thereof secreted by the halophilic bacteria belonging to the genus *Halomonas* may be consumed as a substrate for lactic acid fermentation by the same lactic acid bacteria, and the pH of the culture medium may be further reduced.

Accordingly, in order to culture the halophilic bacteria belonging to the genus *Halomonas* in a non-sterilized medium and/or a non-sterilized environment to produce 3-hydroxybutyric acid or a salt thereof, the pH of the medium is preferably adjusted and maintained at about 8.5 or more in step c.

Examples of pH adjusters include, but are not particularly limited to, hydroxide, carbonate, hydrogen carbonate, and the like. Specific examples include sodium hydroxide, potassium hydroxide, calcium hydroxide, magnesium hydroxide, sodium carbonate, potassium carbonate, calcium carbonate, magnesium carbonate, sodium hydrogen carbonate, potassium hydrogen carbonate, calcium hydrogen carbonate, magnesium hydrogen carbonate, and the like. Of these, those that are weakly alkaline are preferred, and sodium hydrogen carbonate is most preferred.

Even in the invention according to the third embodiment, it is preferable that urea is used as the nitrogen source to be contained in the medium.

Fourth Embodiment

The process for producing 3-hydroxybutyric acid or a salt thereof according to the present invention also includes an embodiment in which a step of adjusting and/or maintaining the pH of the culture medium at 7 or more is added to the second embodiment. Examples of this embodiment include a production process comprising the following steps (A) to (E) (this is referred to as the fourth embodiment in the present specification):

(A) step A of culturing one or more halophilic bacteria belonging to the genus *Halomonas* under aerobic conditions in a medium containing an organic carbon source and an inorganic salt;

(B) step B of adding at least one member selected from the group consisting of nitrogen sources, metal salts, and borate to the culture medium of step A;

(C) step C of changing the culture conditions from aerobic culture to microaerobic culture after step B, and culturing bacterial ceils of the halophilic bacteria;

(D) step D of adjusting and/or maintaining the pH of the culture medium at 7 or more, and causing the bacterial cells to produce 3-hydroxybutyric acid or a salt thereof in a culture medium; and (E) step E of collecting the 3-hydroxybutyric acid or the salt thereof from the culture medium obtained in step D.

Step D of the fourth embodiment can be the same as step c of the third embodiment, and step E can be the same as step d of the third embodiment.

Even in the invention according to the fourth embodiment, it is preferable that urea is used as the nitrogen source to be contained in the medium.

The invention according to the fourth embodiment can generally produce about 40 g or more of 3-hydroxybutyric acid or salt thereof per liter of the medium.

Fifth Embodiment

The process for producing 3-hydroxybutyric acid or a salt thereof according to the present invention also includes a fifth embodiment in which a step of reducing the volume of the culture medium is added to the first embodiment.

Examples of this embodiment include a production process comprising the following steps (I) to (IV):

(I) step I of culturing one or more halophilic bacteria belonging to the genus Halomonas under aerobic conditions in a medium containing an organic carbon source and an inorganic salt;

(II) step II of reducing the volume of the culture medium obtained in step I;

(III) step III of changing the culture conditions in step II from aerobic culture to microaerobic culture, and culturing bacterial cells of the halophilic bacteria to produce 3-hydroxybutyric acid or a salt thereof in a culture medium; and (IV) step IV of collecting the 3-hydroxybutyric acid or the salt thereof from the culture medium obtained in step III.

Step I can be the same as step 1 of the first embodiment, step III can be the same as step 2 of the first embodiment, and step IV can be the same as step 3 of the first embodiment.

Specific examples of the step of reducing the volume of the culture medium (step II) include a means for separating the culture in step I into the culture medium (liquid fraction) and the cultured halophilic bacterial cells belonging to the genus *Halomonas* (solid fraction), removing part of the liquid fraction, then resuspending the solid fraction, and restarting the culture.

There is also another means in which after the solid fraction is separated, the separated solid fraction is resuspended using a medium obtained by newly preparing the medium used in step I in an amount smaller than the volume of the liquid fraction, and the culture is then restarted.

The means for separating the culture medium and the cultured halophilic bacterial cells belonging to the genus *Halomonas* is not particularly limited. For example, a known solid-liquid separation method, such as centrifugation, filtration, or still standing, may be used.

Even in the invention according to the firth embodiment, it is preferable that urea is used as the nitrogen source to be contained in the medium.

Sixth Embodiment

The second embodiment may also comprise a step of reducing the volume of the culture medium. Examples of such an embodiment include a production process comprising the following steps (A) to (E) (this is referred to as the sixth embodiment in the present specification):

(A) step A of culturing one or more halophilic bacteria belonging to the genus *Halomonas* under aerobic conditions in a medium containing an organic carbon source and an inorganic salt;

(B) step B of adding at least one member selected from the group consisting of nitrogen sources, metal salts, and borate to the culture medium of step A;

(C) step C of reducing the volume of the culture medium obtained in step B;

(D) step D of changing the culture conditions from aerobic culture to microaerobic culture after step C, and culturing bacterial cells of the halophilic bacteria to produce 3-hydroxybutyric acid or a salt thereof in a culture medium; and (E) step E of collecting the 3-hydroxybutyric acid or the salt thereof from the culture medium obtained in step D.

Step C of the sixth embodiment can be the same as step II of the fifth embodiment, step D can be the same as step C of the second embodiment, and step E can be the same as step D of the second embodiment.

In step C of the sixth embodiment, the specific means for reducing the volume of the culture medium is, as described in step II of the fifth embodiment above, such that after the solid fraction is separated, the separated solid fraction is resuspended using a medium obtained by newly preparing the medium used in step A of the sixth embodiment so as to contain at least one member selected from the group consisting of nitrogen sources, metal salts, and borate to be added in step B of the sixth embodiment, in an amount smaller than the volume of the liquid fraction, and the culture is then restarted.

Even in the invention according to the sixth embodiment, it is preferable that urea is used as the nitrogen source to be contained in the medium.

Seventh Embodiment

Moreover, the third embodiment may also comprise a step of reducing the volume of the culture medium. Examples of such an embodiment include a production process comprising the following steps (a) to (e) (this is referred to as the seventh embodiment in the present specification):

(a) step a of culturing one or more halophilic bacteria belonging to the genus *Halomonas* under aerobic conditions in a medium containing an organic carbon source and an inorganic salt;

(b) step b of reducing the volume of the culture medium;

(c) step c of changing the culture conditions from aerobic culture to microaerobic culture after step b;

(d) step d of adjusting and/or maintaining the pH of the culture medium at 7 or more after step c, and causing the bacterial cells to produce 3-hydroxybutyric acid or a salt thereof in a culture medium; and (e) step e of collecting the 3-hydroxybutyric acid or the salt thereof from the culture medium obtained in step d.

Step b of the seventh embodiment can be the same as step II of the fifth embodiment, step c can be the same as step b of the third embodiment, step d can be the same as step c of the third embodiment, and step e can be the same as step d of the third embodiment.

Even in the invention according to the seventh embodiment, it is preferable that urea is used as the nitrogen source to be contained in the medium.

Eighth Embodiment

Furthermore, the fourth embodiment may also comprise a step of reducing the volume of the culture medium. Examples of such an embodiment include a production process comprising the following steps (A) to (F) (this is referred to as the eighth embodiment in the present specification):

(A) step A of culturing one or more halophilic bacteria belonging to the genus *Halomonas* under aerobic conditions in a medium containing an organic carbon source and an inorganic salt;

(B) step B of adding at least one member selected from the group consisting of nitrogen sources, metal salts, and borate to the culture medium of step A;

(C) step C of reducing the volume of the culture medium;

(D) step D of changing the culture conditions from aerobic culture to microaerobic culture after step C, and culturing bacterial cells of the halophilic bacteria;

(E) step E of adjusting and/or maintaining the pH of the culture medium at 7 or more after step D, and causing the bacterial cells to produce 3-hydroxybutyric acid or a salt, thereof in a culture medium; and (F) step F of collecting the 3-hydroxybutyric acid or the salt thereof from the culture medium obtained in step E.

Step C of the eighth embodiment can be the same as step II of the fifth embodiment, step D can be the same as step C of the fourth embodiment, step E can be the same as step D of the fourth embodiment, and step F can be the same as step E of the fourth embodiment.

The degree of reducing the volume of the culture medium is not particularly limited. For example, when the concentration of the cultured halophilic bacterial cells belonging to the genus *Halomonas* in the culture medium is about two times higher than the concentration before the volume of the culture medium is reduced, the yield of 3-hydroxybutyric acid or salt thereof to be obtained is expected to exceed about 100 g/L. Moreover, when the concentration is 4 times higher, the yield is expected to exceed 250 g/L.

Even in the invention according to the eighth embodiment, it is preferable that urea is used as the nitrogen source to be contained in the medium.

The present invention is described in more detail below with reference to Examples. Needless to say, the present invention is not limited to the Examples.

EXAMPLES

In the Examples, a process for producing 3-hydroxybutyric acid or a salt thereof using halophilic bacteria belonging to the genus *Halomonas* is described in detail.

A medium based on the modified SOT 5 (modified *Spirulina platensis* medium 5 shown in Table 1 was used. This medium was a *Spirulina platensis* medium (website of the National Institute for Environmental Studies), in which the amounts of $NaHCO_3$ and $Na_2CO_3$ were adjusted, the amount of $NaNO_3$ as a nitrogen source was increased by 5 times, and the amount of $K_2HPO_4$ as a phosphorus source was increased by 4 times. The pH of the medium after adjustment was 9.4±0.1. The medium was used as it is, without sterilization by using an autoclave, etc.

Various organic carbon sources were suitably added to the above medium during culture. The specific organic carbon source used was glucose with a final concentration in the medium of 20% or 25%.

TABLE 1

| Modified SOT 5 medium | | | |
|---|---|---|---|
| $NaHCO_3$ | 1.26 g | $Na_2CO_3$ | 0.53 g |
| $K_2HPO_4$ | 200 mg | $NaCO_3$ | 1250 mg |
| $K_2SO_4$ | 100 mg | NaCl | 100 mg |
| $MgSO_4 \cdot 7H_2O$ | 20 mg | $CaCl_2 \cdot 2H_2O$ | 4 mg |
| $FeSO_4 \cdot 7H_2O$ | 1 mg | $Na_2$ EDTA | 8 mg |
| A5 + Co solution | 0.1 ml | Distilled water | 100 mL |
| A5 + Co solution | | | |
| $H_3BO_3$ | 2.86 mg | $MnSO_4 \cdot 7H_2O$ | 250 mg |
| $ZnSO_4 \cdot 2H_2O$ | 22.2 m | $CuSO_4 \cdot 5H_2O$ | 7.9 mg |
| $Na_2MoO_4 \cdot 2H_2$ | 2.1 mg | $Co(No_3) \cdot 6H_2$ | 4.398 mg |
| Distilled water | 100 mL | | |

Measurement of 3-Hydroxybutyric Acid or Salt thereof

In the Examples, the production, of 3-hydroxybutyric acid or a salt thereof in a culture medium was measured by the following method to which the technique of polyhydroxyalkanoate (PHA) analysis described in NPL 3 was applied.

After a culture medium was centrifuged, only the supernatant was taken, and 50 μL of the supernatant was dried. Methanol (0.50 ml) containing 3 vol % $H_2SO_4$ was added to the dried supernatant, and the mixture was heated at 105° C. for 1 hour to completely convert 3-hydroxybutyric acid or a salt thereof to methyl 3-hydroxybutyrate.

After the mixture was cooled to room temperature, 0.50 ml of chloroform and 0.25 ml of distilled water were added, and the mixture was vigorously stirred. After centrifugation for one minute, 1 μl of chloroform layer was taken as a sample. Then, the amount of 3-hydroxybutyric acid in the sample was measured using a gas chromatography apparatus.

On the other hand, a standard of 3-hydroxybutyric acid was treated in the same manner as the dried supernatant. Based on the standard, the 3-hydroxybutyric acid accumulation rate per liter of the medium (3-hydroxybutyric acid (g)/supernatant liquid (L)) was calculated. The value measured by using an "F-kit D-3-hydroxybutyric acid" kit (J. K. International Inc.), which detects only D-isomers, matched the value measured by using the gas chromatography apparatus. This confirmed that almost all of the secreted 3-hydroxybutyric acid was D-isomer.

Measurement of PHB Accumulation Rate

In the Examples, the amount of PHB accumulated in the bacterial cells was measured in the following manner suitably using the technique described in NPL 1.

The culture medium obtained above was centrifuged to obtain the bacterial cells alone, and the cells were washed with distilled water several times and then dried. Methanol (0.50 ml) containing 3 vol % $H_2SO_4$ was added to 1 to 3 mg of the dry cells, and heated at 105° C. for 3 hours. After the mixture was cooled to room temperature, 0.50 ml of chloroform and 0.25 ml of distilled water were added and vigorously stirred.

After centrifugation for one minute, 1 µl of chloroform layer was taken as a sample. Then, the amount of PHB in the sample was measured using a gas chromatography apparatus.

On the other hand, a standard of PHB was treated in the same manner as for the dry cells. Based on the standard, the PHB accumulation rate per dry cell (PHB (g)/dry cell weight (g)) was calculated.

Pre-culture of Halophilic Bacteria Belonging to Genus *Halomonas*

After plate culture of halophilic bacteria belonging to the genus *Halomonas* (*Halomonas* sp. KM-1 strain), 1 w/v % glucose, rather than the above-mentioned glucose, was added as a carbon source to 5 ml of the above modified SOT 5 medium placed in a test tube (diameter: 16.5 mm), and culture with shaking at 37° C. was carried out overnight.

Culture of Halophilic Bacteria Belonging to Genus *Halomonas*, Collection of Samples, etc.

Production Example 1

The pre-cultured halophilic bacterial cells belonging to the genus *Halomonas* (0.2 ml) were seeded in 20 ml of the modified SOT 5 medium placed in a 100-ml Erleumeyer flask, and the flask was closed with Silicosen. Culture with shaking was carried out at 33° C. at a stirring rate of 200 rpm. After 24 hours, 0.5 ml of culture medium was collected at intervals of about 12 hours, and the amount of 3-hydroxybutyric acid or salt thereof in the supernatant was measured.

As the organic carbon source, glucose was added to the medium so that the final concentration was 20 wt. %.

At the beginning of culture, the cells were cultured under aerobic conditions at a stirring rate of 200 rpm. After 60 hours, the conditions were changed to microaerobic conditions at a stirring rate of 50 rpm. After sampling the culture medium, the flask was again closed with Silicosen, and culture with shaking at 33° C. was continued for batch culture.

Further, as the nitrogen source, 12.5 g/L of sodium nitrate was added at the beginning of culture; 2.5 g/L was added at the 24th hour after the start of culture; 2.5 g/L was added at the 24th hour and the 36th hour; 2.5 g/L of sodium, nitrate was added at the 24th hour, the 36th hour, and the 48th hour; and no nitrogen source was added. These results were compared. FIGS. 1 to 4 show the results.

As shown in the results of FIG. 1, 3-hydroxybutyric acid was not secreted when the aerobic conditions were simply changed to microaerobic conditions after 60 hours without adding sodium nitrate.

In contrast, when sodium nitrate was added after 24 hours, 3-hydroxybutyric acid was secreted in the culture supernatant after 72 hours. When the nitrogen source was added after 24 hours and 36 hours, and when sodium nitrate was added after 24 hours, 36 hours, and 48 hours, a larger amount of 3-hydroxybutyric acid was secreted.

These results revealed that 3-hydroxybutyric acid was not sufficiently produced in the culture supernatant simply by changing the culture conditions from aerobic culture to microaerobic culture, and that it was necessary to add a suitable nitrogen source, such as sodium nitrate, at a suitable time during aerobic culture.

Production Example 2

As the amount of glucose in Production Example 1, 20 wt. % was added to the medium at the start of culture, and 5 wt. % was further added at the 24th hour after the start of culture.

Moreover, 2.5 g/L of sodium nitrate as a nitrogen source was added 24 boars, 36 hours, and 43 hours after the start of culture.

Further, after 36 hours, an A5+Co solution as a metal salt was added in an amount 1/100 of the amount shown in Table 1 above. This case was compared, with a case in which no A5+Co solution was added. Other conditions were the same as those of Production Example 1. FIGS. 5 to 8 show the results.

Figure 5:
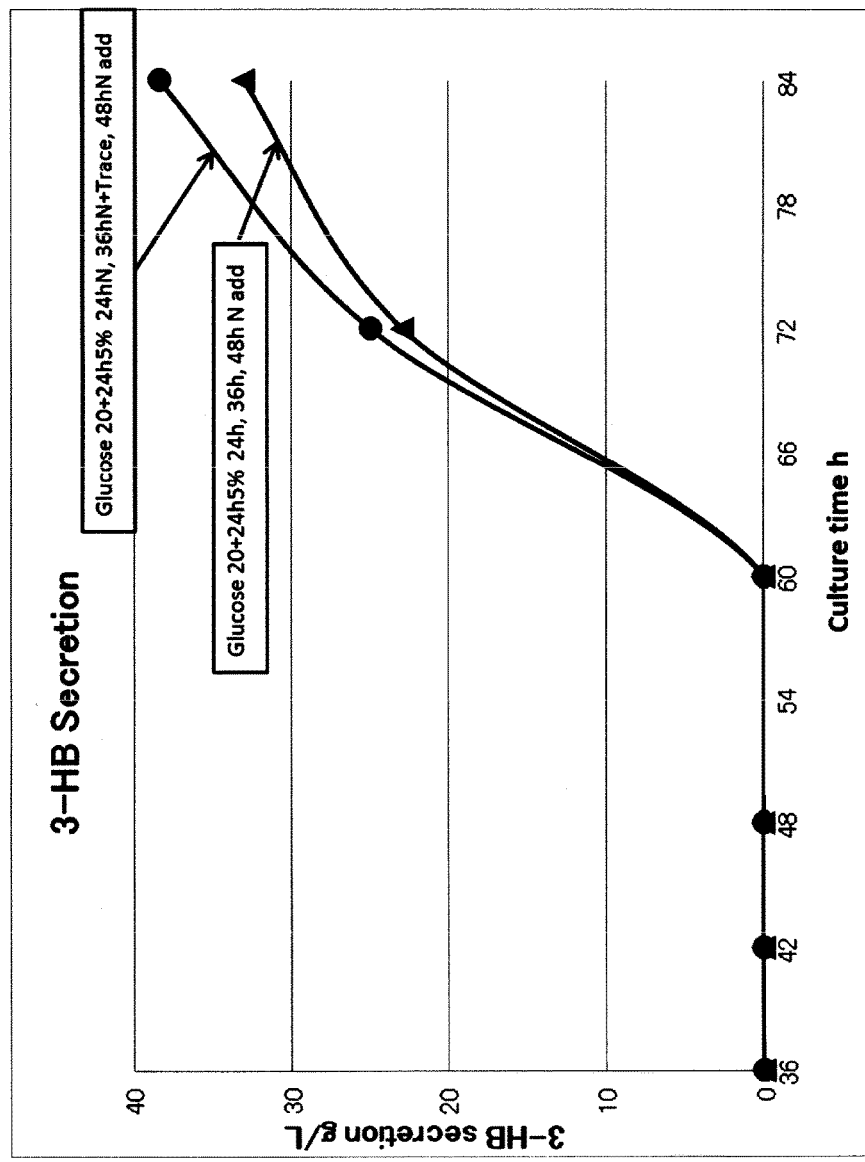
FIG. 5 is a graph showing the ratio of 3-hydroxybutyric acid or a salt thereof accumulated in the culture supernatant (vertical axis: 3-hydroxybutyric acid or a salt thereof (g)/culture supernatant (L), and the culture time (horizontal axis: h)) obtained by the process shown in Production Example 2 in the Examples. Filled circles (●) in the graph show the results when 25%, in total, of glucose was added to a modified SOT 5 medium, and sodium nitrate as a nitrogen source was further added 24 hours, 36 hours, and 48 hours after the start of culture. Filled triangles (▲) in the graph show the results when 25%, in total, of glucose was added to a modified SOT 5 medium, sodium nitrate as a nitrogen source was further added 24 hours and 48 hours after the start of culture, and sodium nitrate as a nitrogen source and a metal salt-containing additive were further added 36 hours after the start of culture.
Figure 6:
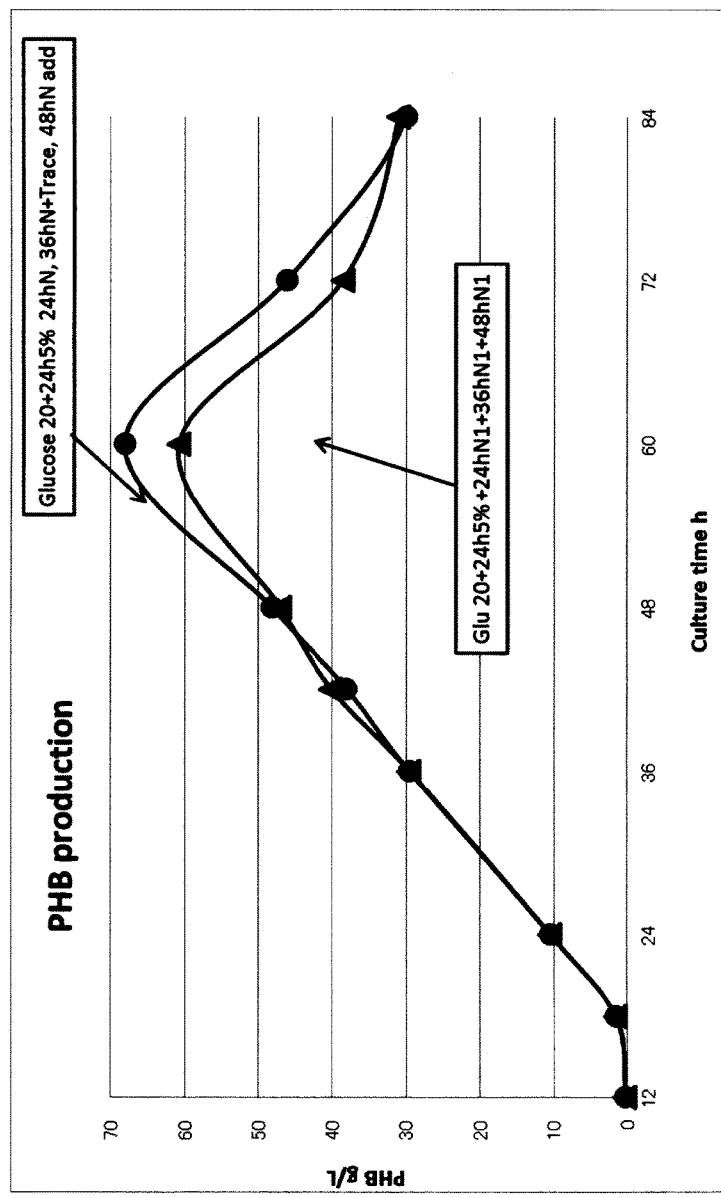
FIG. 6 is a graph showing the amount of PHB (vertical axis: PHB (g)/culture supernatant (L), and the culture time (horizontal axis: h)) obtained by the process shown in Production Example 2 in the Examples. Filled circles (●) in the graph show the results when 25%, in total, of glucose was added to a modified SOT 5 medium, and sodium nitrate as a nitrogen source was further added 24 hours, 36 hours, and 48 hours after the start of culture. Filled triangles (▲) in the graph show the results when 25%, in total, of glucose was added to a modified SOT 5 medium, sodium nitrate as a nitrogen source was further added 24 hours and 48 hours after the start of culture, and sodium nitrate as a nitrogen source and a metal salt-containing additive were further added 36 hours after the start of culture.
Figure 7:
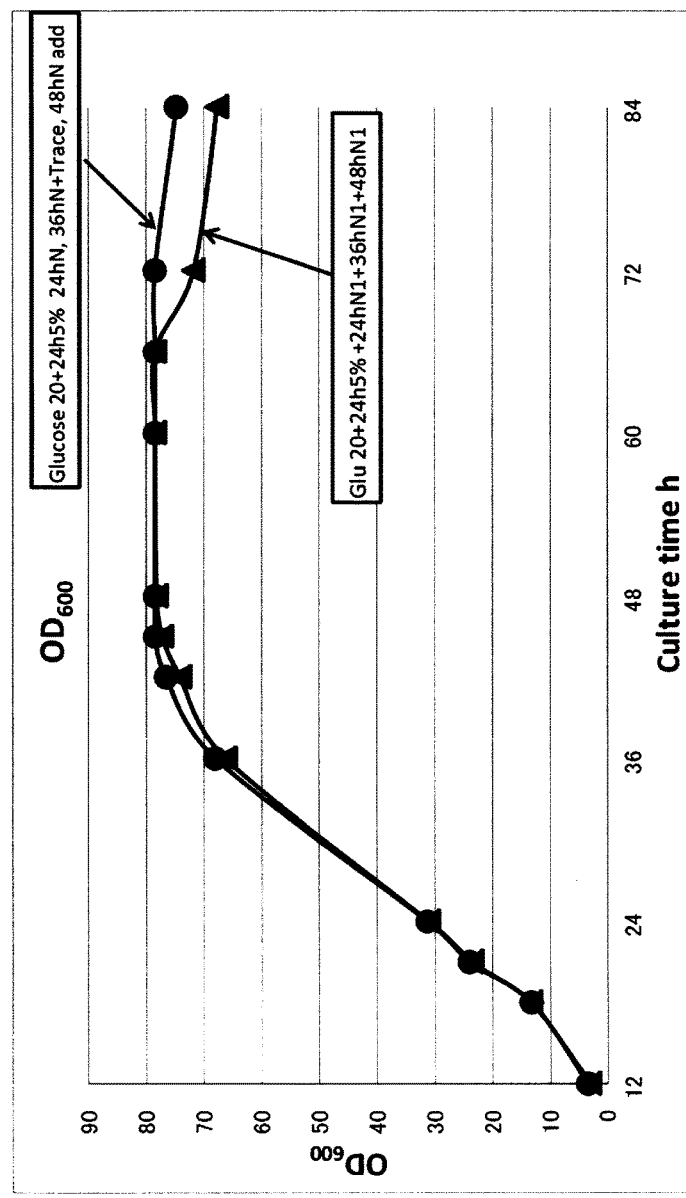
FIG. 7 is a graph showing the amount of bacterial cells (vertical axis: $OD_{600}$, and the culture time (horizontal axis: h)) obtained by the process shown in Production Example 2 in the Examples. Filled circles (●) in the graph show the results when 25%, in total, of glucose was added to a modified SOT 5 medium, and sodium nitrate as a nitrogen source was further added 24 hours, 36 hours, and 48 hours after the start of culture. Filled triangles (▲) in the graph show the results when 25%, in total, of glucose was added to a modified SOT 5 medium, sodium nitrate as a nitrogen source was further added 24 hours and 48 hours after the start of culture, and sodium nitrate as a nitrogen source and a metal salt-containing additive were further added 36 hours after the start of culture.
Figure 8:
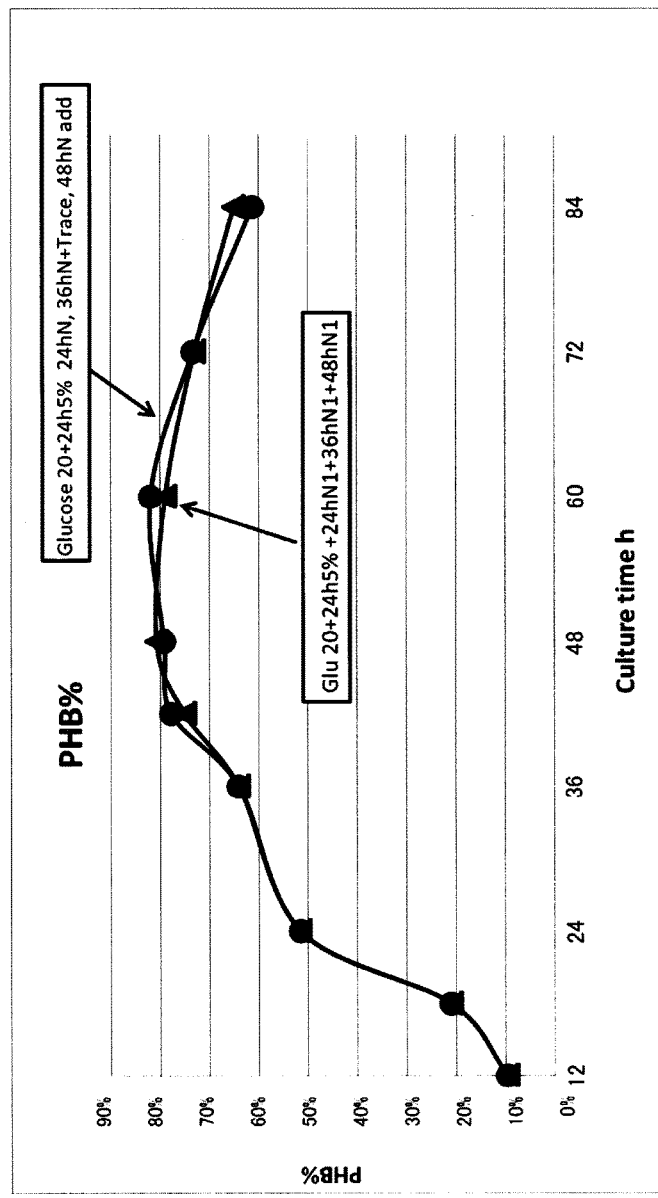
FIG. 8 is a graph showing the amount of PHB accumulated in bacterial cells (vertical axis: PHB (%): PHB (g)/dry cell weight (g), and the culture time (horizontal axis: h)) obtained by the process shown in Production Example 2 in the Examples. Filled circles (●) in the graph show the results when 25%, in total, of glucose was added to a modified SOT 5 medium, and sodium nitrate as a nitrogen source was further added 24 hours, 36 hours, and 48 hours after the start of culture. Filled triangles (▲) in the graph show the results when 25%, in total, of glucose was added to a modified SOT 5 medium, sodium nitrate as a nitrogen source was further added 24 hours and 48 hours after the start of culture, and sodium nitrate as a nitrogen source and a metal salt-containing additive were further added 36 hours after the start of culture.
Figure 9:
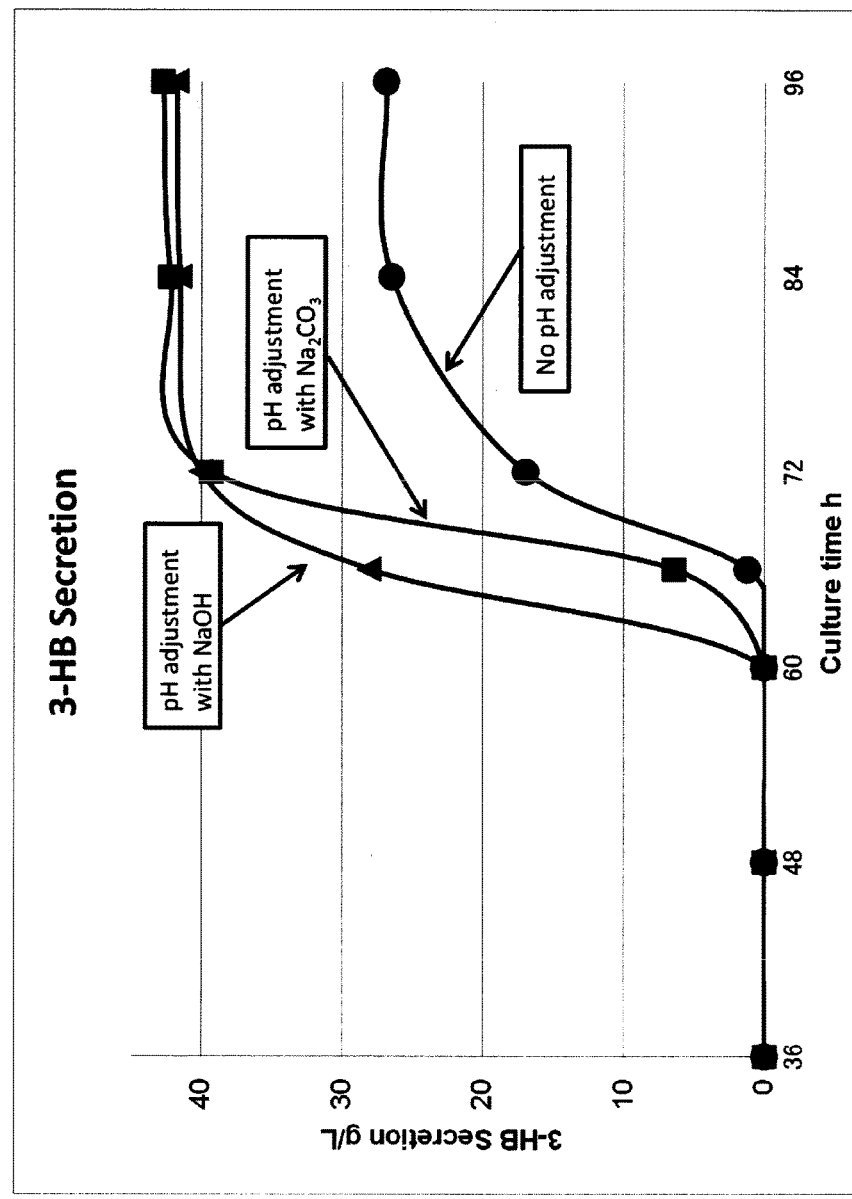
FIG. 9 is a graph showing the ratio of 3-hydroxybutyric acid or a salt thereof accumulated in the culture supernatant (vertical axis: 3-hydroxybutyric acid or a salt thereof (g)/culture supernatant (L), and the culture time (horizontal axis: h)) obtained by adding 20% glucose to a modified SOT 5 medium, performing aerobic culture using a 1-L scale fermenter, then changing the culture conditions to microaerobic conditions after 60 hours, and adjusting the pH using sodium hydroxide or sodium carbonate; and obtained as the control in which the pH was not adjusted, shown in Production Example 3 in the Examples. Filled circles (●) in the graph show the results when the pH was not adjusted during microaerobic culture. Filled triangles (▲) in the graph show the results when the pH was adjusted to 9.0 using sodium hydroxide during microaerobic culture. Filled squares (■) in the graph show the results when the pH was adjusted to 9.0 using sodium carbonate during microaerobic culture.
Figure 10:
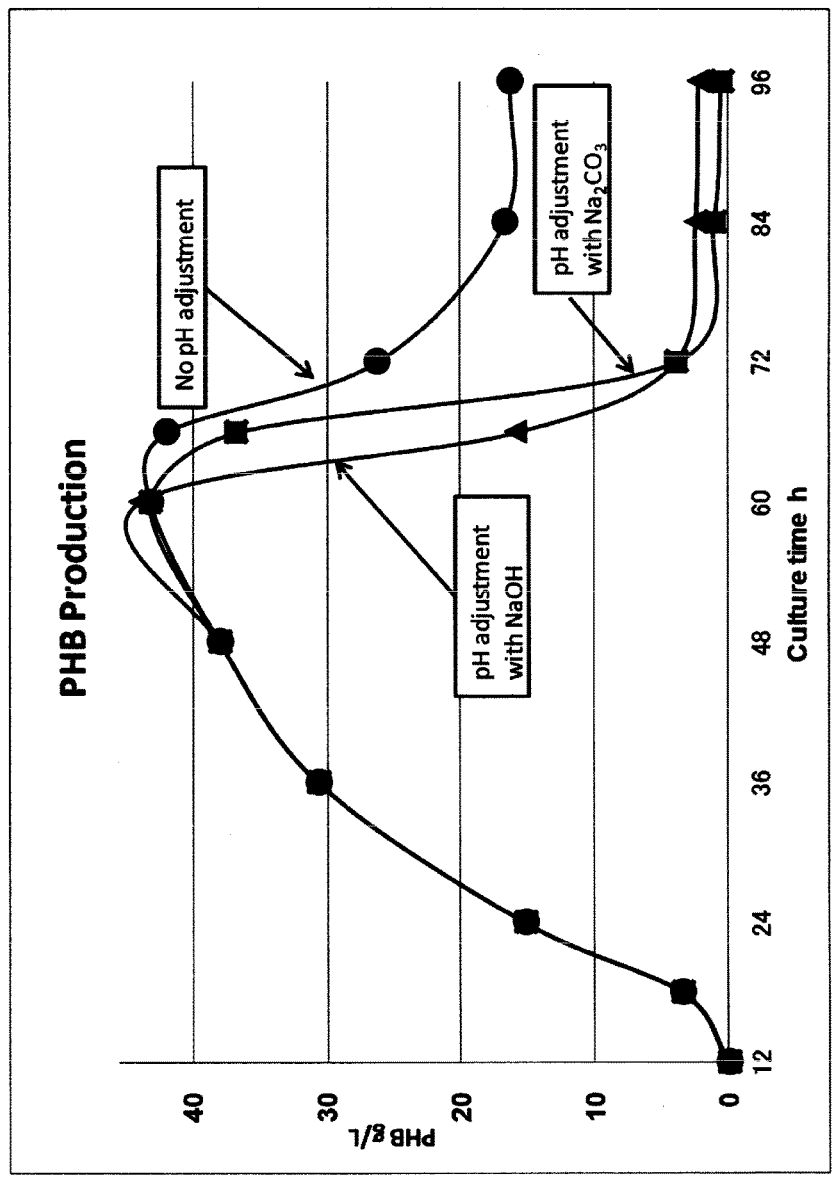
FIG. 10 is a graph showing the amount of PHB (vertical axis: PHB (g)/culture supernatant (L), and the culture time (horizontal axis: h)) obtained by the process shown in Production Example 3 in the Examples. Filled circles (●) in the graph show the results when the pH was not adjusted during microaerobic culture. Filled triangles (▲) in the graph show the results when the pH was adjusted to 9.0 using sodium hydroxide during microaerobic culture. Filled squares (■) in the graph show the results when the pH was adjusted to 9.0 using sodium carbonate during microaerobic culture.
Figure 11:
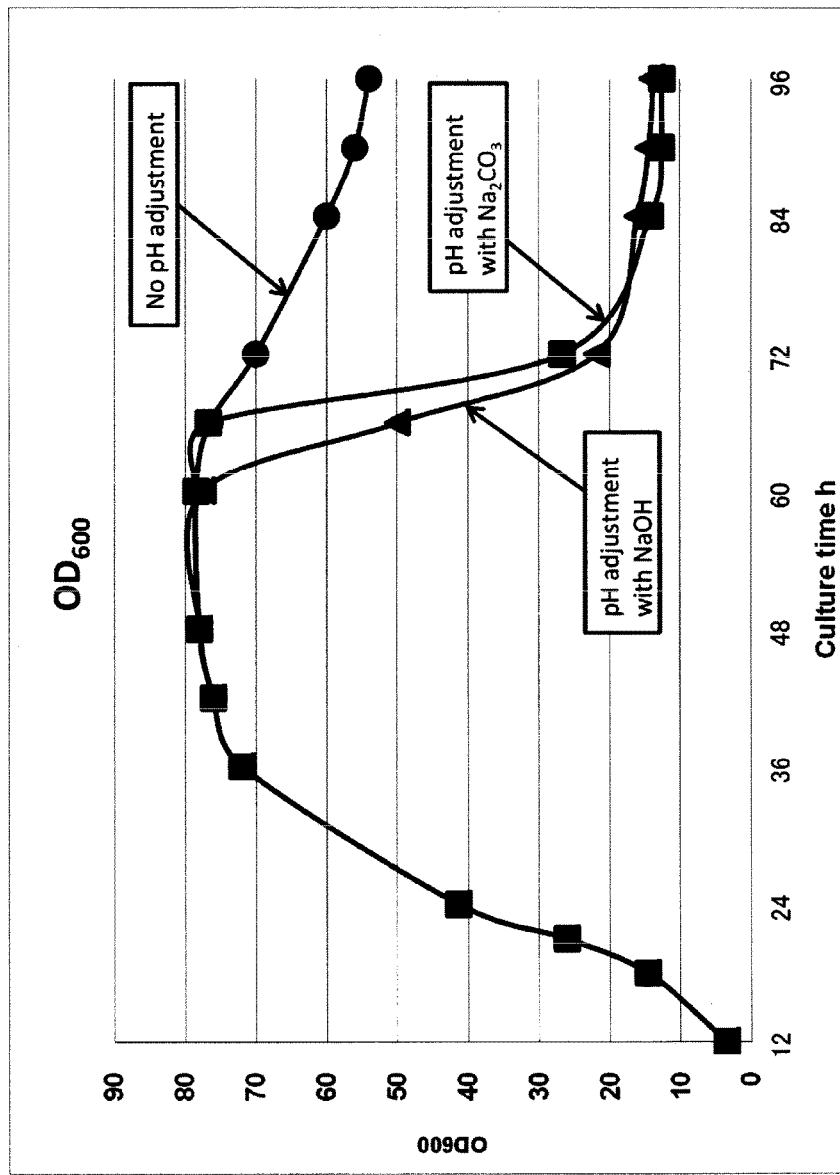
FIG. 11 is a graph showing the amount of bacterial cells (vertical axis: $OD_{600}$, and the culture time (horizontal axis: h)) obtained by the process shown in Production Example 3in the Examples. Filled circles (●) in the graph show the results when the pH was not adjusted during microaerobic culture. Filled triangles (▲) in the graph show the results when the pH was adjusted to 9.0 using sodium hydroxide during microaerobic culture. Filled squares (■) in the graph show the results when the pH was adjusted to 9.0 using sodium carbonate during microaerobic culture.
Figure 12:
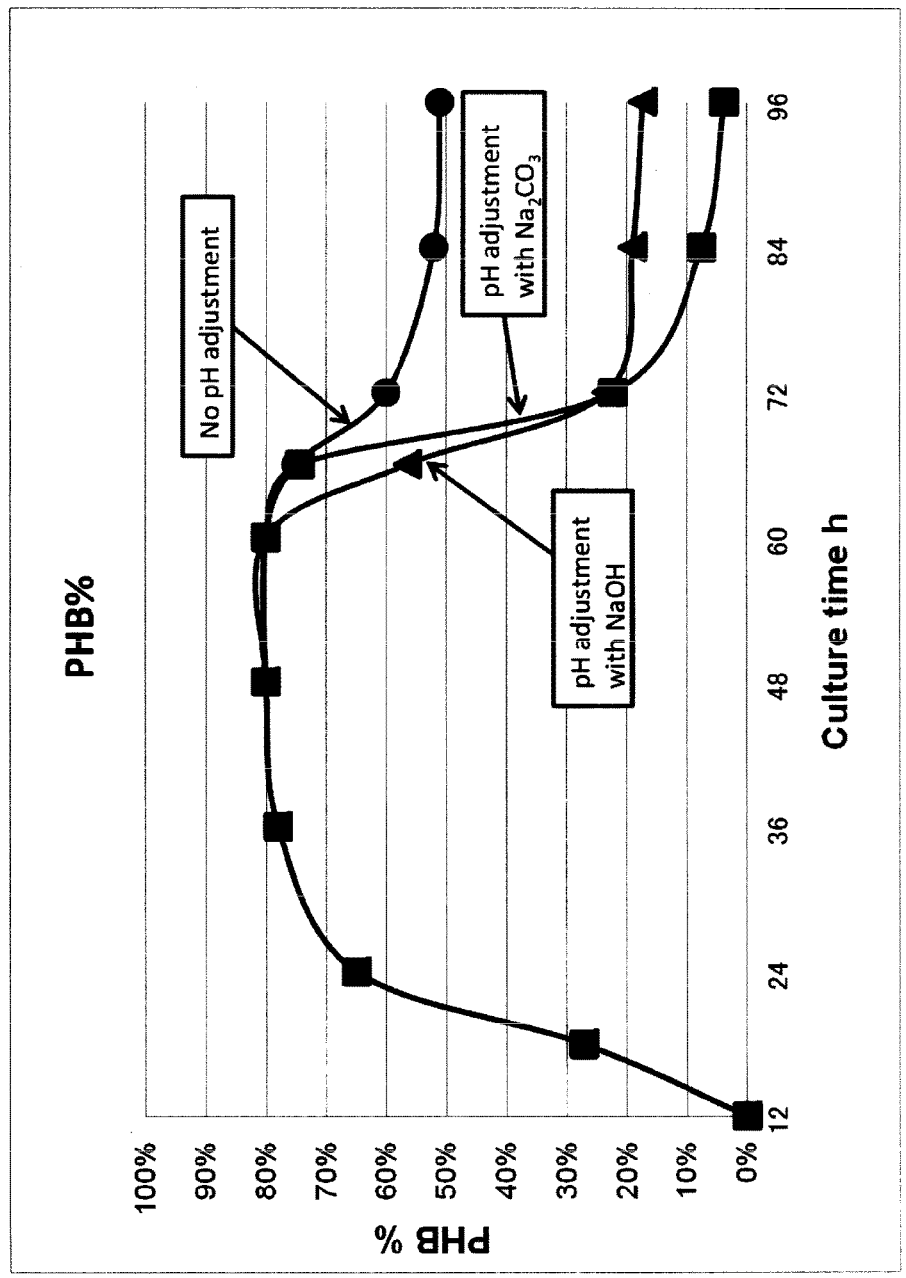
FIG. 12 is a graph showing the amount of PHB accumulated in bacterial cells (vertical axis: PHB (%): PHB (g) / dry cell weight (g), and the culture time (horizontal axis: h)) obtained by the process shown in Production Example 3 in the Examples. Filled circles (●) in the graph show the results when the pH was not adjusted during microaerobic culture. Filled triangles (▲) in the graph show the results when the pH was adjusted to 9.0using sodium hydroxide during microaerobic culture. Filled squares (■) in the graph show the results when the pH was adjusted to 9.0 using sodium carbonate during microaerobic culture.

As shown in the results of FIG. 5, even when the total amount of glucose was 25 wt. %, a remarkable amount of 3-hydroxybutyric acid was secreted in the culture supernatant at the 72nd hour after the start of culture, as in Production Example 1, in which the total amount of glucose was 20 wt. %.

It was also revealed that when the metal salt was added after 36 hours, a larger amount of 3-hydroxybutyric acid was secreted and produced in the culture supernatant, compared with when no metal salt was added.

Production Example 3

The pre-cultured halophilic bacterial cells belonging to the genus *Halomonas* (0.5 ml) were seeded in 20 ml of the modified SOT 5 medium (containing 20% glucose) placed in a 200-ml Erlenmeyer flask, and the flask was closed with Silicosen. Culture with shaking was carried out under aerobic culture conditions at 33° C. at a stirring rate of 200 rpm for 36 hours. The resulting cells were used as a seed strain.

The modified SOT 5 medium (containing 20% glucose; 500 mL) was added to a 1-L scale fermenter, and the conditions were adjusted to 33° C. and DO30%. The above seed strain (5 mL; equivalent to about 1%) was seeded, and culture was started. Thereafter, DO was reduced to 10% after 24 hours. Further, as the nitrogen source, 12.5 g/L of sodium nitrate was contained at the beginning of culture, and 2.5 g/L of sodium nitrate was further added at the 24th hour, the 36th hour, and the 48th hour after the start of culture.

In addition, air supply was stopped after 60 hours, and DO was adjusted to 0.5% or less only by stirring. Thereafter, although the pH decreased along with the secretion and production of 3-hydroxybutyric acid, the pH was adjusted to 8.5 using sodium hydroxide or sodium carbonate. This was compared with when the pH was not adjusted. FIGS. 9 to 12 show the results.

These results indicate that when the pH was adjusted to 8.5 using sodium hydroxide or sodium carbonate, the degradation of PHB was faster and more significant (about 80% was degraded for about 12 hours), as compared with when the pH was not adjusted. Along with the degradation, 3-hydroxybutyric acid was secreted. It was revealed that the pH adjustment of the medium under microaerobic conditions was significantly involved in the degradation of PHB, and the secretion and production, of 3-hydroxybutyric acid in the culture supernatant.

Production Example 4

The pre-cultured halophilic bacterial cells belonging to the genus *Halomonas* (0.5 ml) were seeded in 20 ml of the modified SOT 5 medium (containing 20% glucose) placed in a 200-ml Erlenmeyer flask, and the flask was closed with Silicosen. Culture with shaking was carried out under aerobic culture conditions at 33° C. at a stirring rate of 200 rpm for 36 hours. The resulting cells were used as a seed strain.

The modified SOT 5 medium (containing 20% glucose; 500 mL) was added to a 1-L scale fermenter, and the conditions were adjusted to 33° C. and DO30%. The above seed strain (5 mL; equivalent to about 1%) was seeded, and culture was started. Thereafter, DO was reduced to 10% after 24 hours. Further, as the nitrogen source, 12.5 g/L of sodium nitrate was contained at the beginning of culture, and 2.5 g/L of sodium nitrate was further added at the 24th hour, the 36th hour, and the 48th hour after the start of culture.

Figure 13:
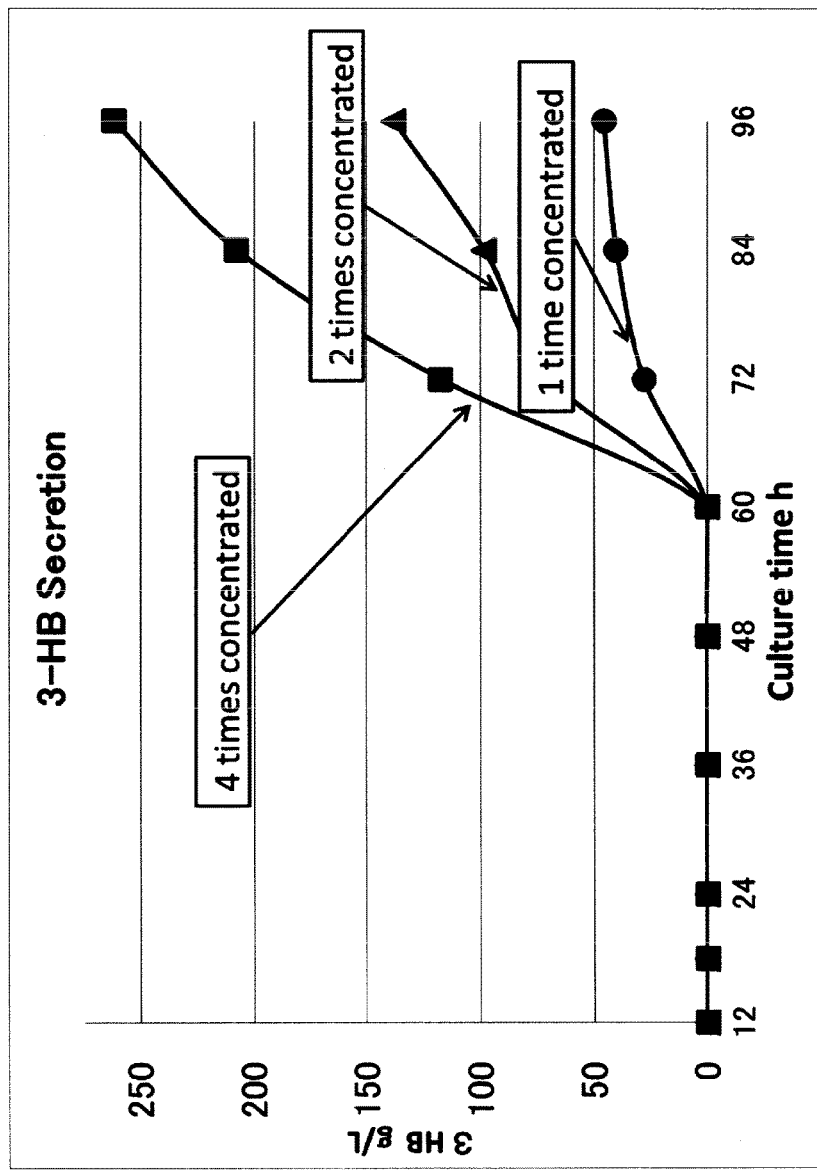
FIG. 13 is a graph showing the ratio of 3-hydroxybutyric acid or a salt thereof accumulated in the culture supernatant (vertical axis: 3-hydroxybutyric acid or a salt thereof (g)/culture supernatant (L), and the culture time (horizontal axis: h)) obtained by adding 20% glucose to a modified SOT 5 medium, performing aerobic culture using a 1-L scale fermenter for 60 hours, then concentrating the culture medium by centrifugation to 1/2 volume, 1/4 volume, and 1/1 volume (control), changing the culture conditions to microaerobic conditions, and adjusting the pH using sodium carbonate, shown in Production Example 4 in the Examples. Filled circles (●) in the graph show the results when the culture was directly changed to microaerobic culture at 1/1 volume as the control. Filled triangles (▲) in the graph show the results when the culture was changed to microaerobic culture after the culture medium was concentrated to 1/2 volume. Filled squares (■) in the graph show the results when the culture was changed to microaerobic culture after the culture medium was concentrated to 1/4 volume.
Figure 14:
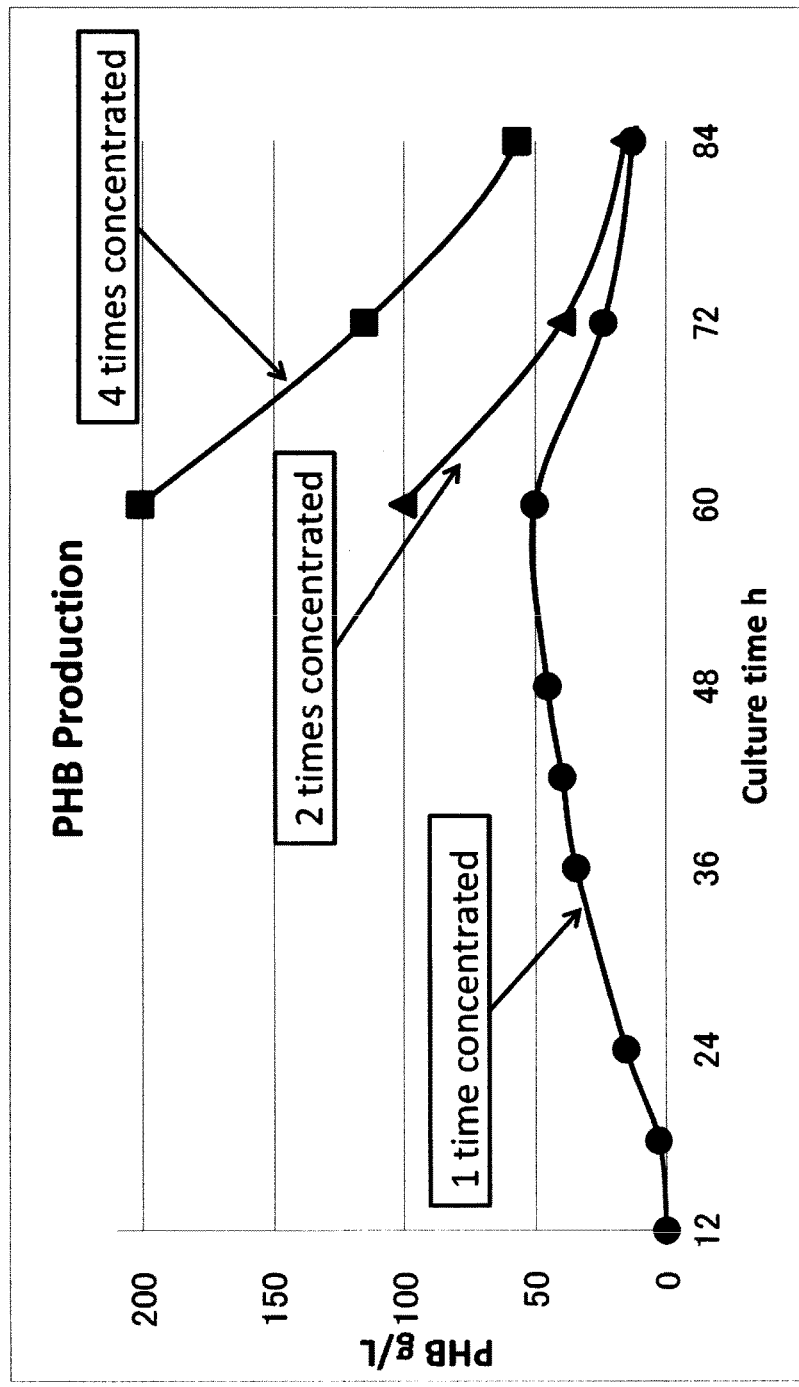
FIG. 14 is a graph showing the amount of PHB (vertical axis: PHB (g)/culture supernatant (L), and the culture time (horizontal axis: h)) obtained by the process shown in Production Example 4 in the Examples. Filled circles (●) in the graph show the results when the culture was directly changed to microaerobic culture at 1/1 volume as the control. Filled triangles (▲) in the graph show the results when the culture was changed to microaerobic culture after the culture medium was concentrated to 1/2 volume. Filled squares (●) in the graph show the results when the culture was changed to microaerobic culture after the culture medium was concentrated to 1/4 volume.

In addition, the bacterial cells and the medium supernatant were separated by centrifugation after 60 hours. The medium supernatant was removed so that the concentration of the halophilic bacterial cells belonging to the genus *Halomonas* among the medium components was two times or four times higher, or equivalent to that before centrifugation. Then, the bacterial cells were resuspended. Subsequently, the resuspension was placed again in the fermenter, air supply was stopped, and DO was adjusted to 0.5% or less only by stirring. Thereafter, although the pH decreased along with the secretion and production of 3-hydroxybutyric acid, the pH was adjusted to 8.5 using sodium carbonate. The results were compared. FIGS. 13 and 14 show the results.

These results show that, in general, when the concentration of a product increases, the production reaction is suppressed by product inhibition; however, in the present Examples, the concentration of 3-hydroxybutyric acid reached 45 g/L, 130 g/L, and 250 g/L, respectively, at 1/1 concentration, 1/2 concentration, and 1/4 concentration. It was also revealed that even when the bacterial cells were highly concentrated, PHB was degraded, and 3-hydroxybutyric acid was secreted and produced in the culture supernatant.

Production Example 5

The pre-cultured halophilic bacterial cells belonging to the genus *Halomonas* (0.2 ml) were seeded in 20 ml of the modified SOT 5 medium (free from a nitrogen source) placed in a 200-ml Erlenmeyer flask, and the flask was closed with Silicosen. As the nitrogen source, 12.5 g/L or 15.0 g/L of sodium nitrate, or 8.75 g/L or 10.5 g/L of urea was added thereto. Culture with shaking was carried out at 33° C. at a stirring rate of 200 rpm. After 24 hours, 0.5 ml of culture medium was collected at intervals of about 12 hours, and the amount of 3-hydroxybutyric acid or salt thereof in the supernatant was measured.

As the organic carbon source, glucose was added to the medium, so that the final concentration was 12 wt. %.

Figure 15:
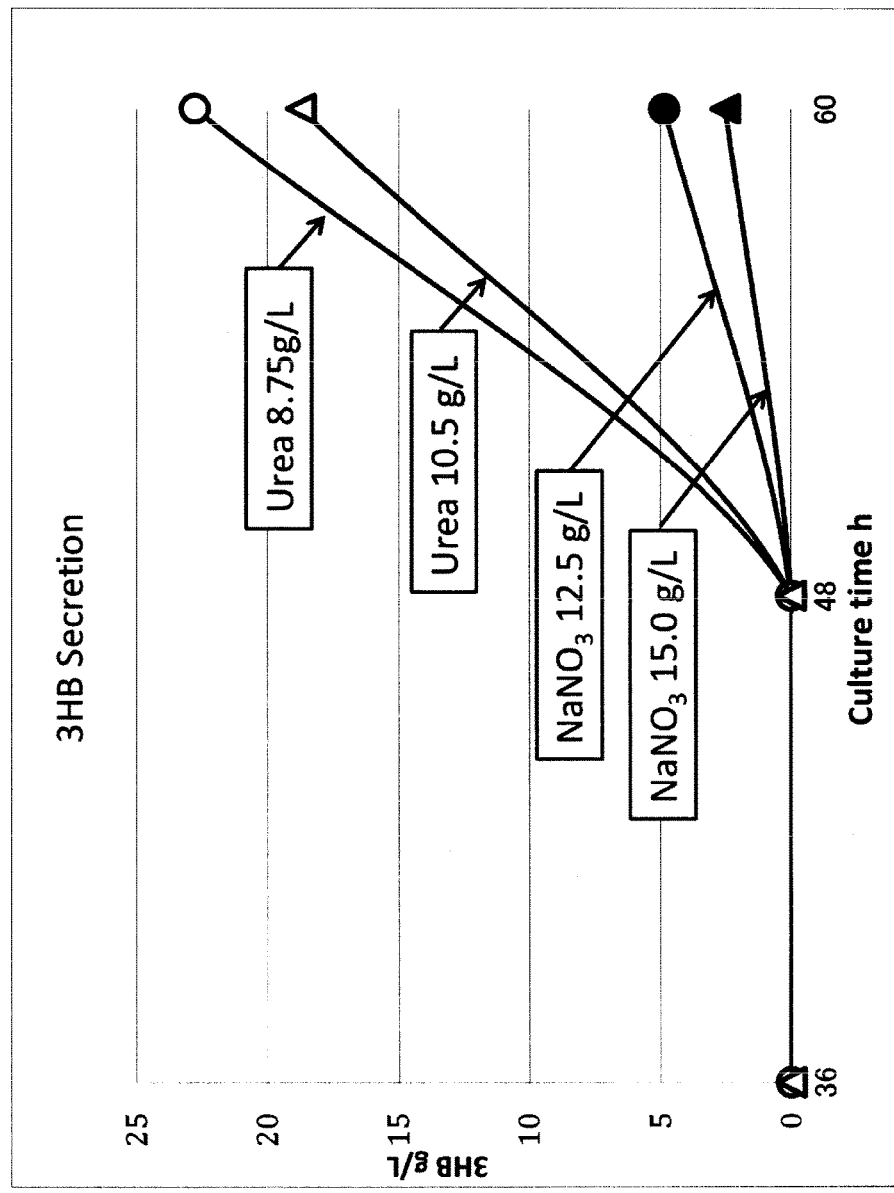
FIG. 15 is a graph showing the ratio of 3-hydroxybutyric acid or a salt thereof accumulated in the culture supernatant (vertical axis: 3-hydroxybutyric acid or a salt thereof (g)/culture supernatant (L), and the culture time (horizontal axis: h)) obtained by culturing by adding 12% glucose to a modified SOT 5 medium (free from a nitrogen source), and adding nitrogen sources with different concentrations, shown in Production Example 5 in the Examples. Filled circles (●) in the graph show the results when 12.5 g/L sodium nitrate was added to a modified SOT 5 medium (free from a nitrogen source). Filled triangles (▲) in the graph show the results when 15.0 g/L sodium nitrate was added to a modified SOT 5 medium (free from a nitrogen source). Open circles (○) in the graph show the results when 8.75 g/L urea was added to a modified SOT 5 medium (free from a nitrogen source). Open triangles (Δ) in the graph show the results when 10.5 g/L urea was added to a modified SOT 5 medium (free from a nitrogen source).
Figure 16:
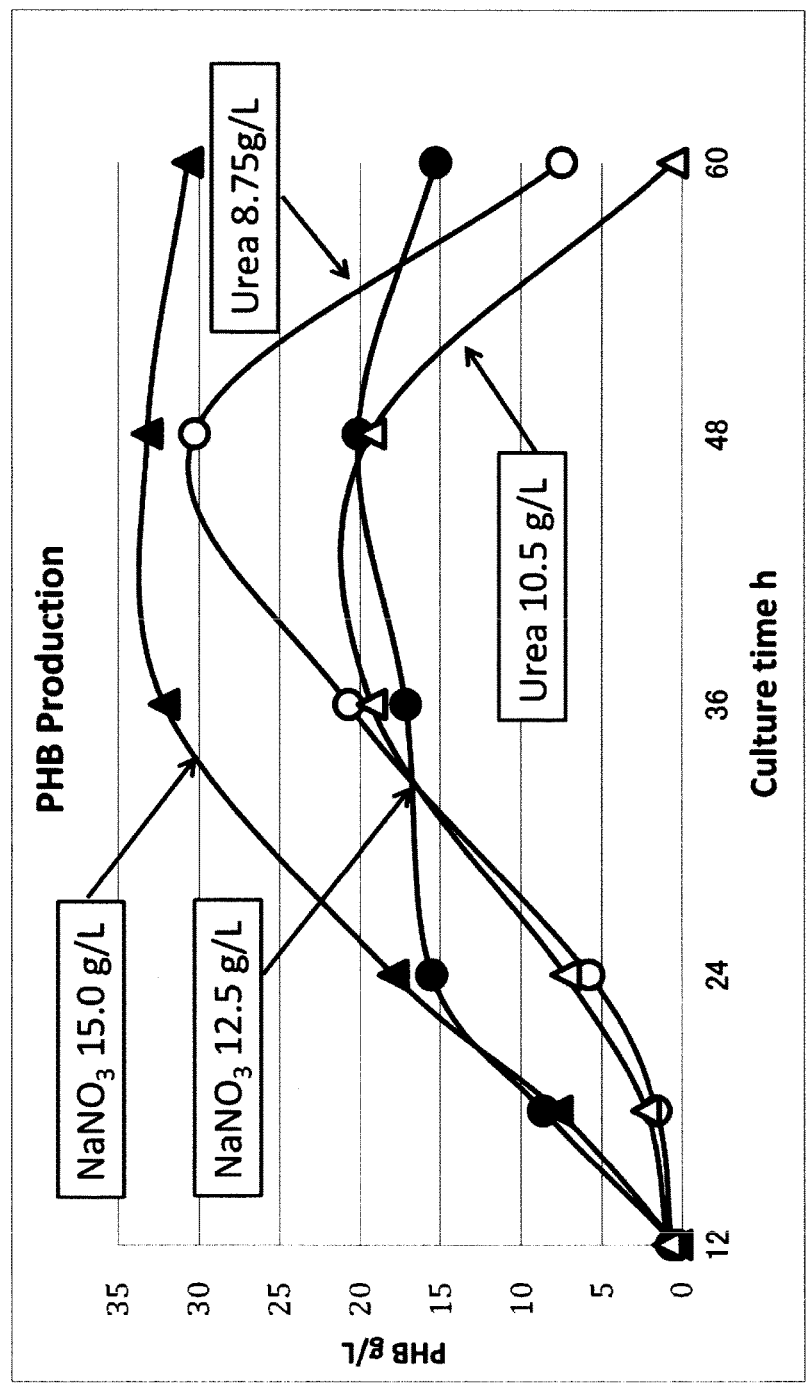
FIG. 16 is a graph showing the amount of PHB accumulated in bacterial cells (vertical axis: PHB (g)/dry cell weight (g), and the culture time (horizontal axis: h)) obtained by culturing by adding 12% glucose to a modified SOT 5 medium (free from a nitrogen source), and adding nitrogen sources with different concentrations, shown in Production Example 5 in the Examples. Filled circles (●) in the graph show the results when 12.5 g/L sodium nitrate was added to a modified SOT 5 medium (free from a nitrogen source). Filled triangles (▲) in the graph show the results when 15.0 g/L sodium nitrate was added to a modified SOT 5 medium (free from a nitrogen source). Open circles (○) in the graph show the results when 8.75 g/L urea was added to a modified SOT 5 medium (free from a nitrogen source). Open triangles (Δ) in the graph show the results when 10.5 g/L urea was added to a modified SOT 5 medium (free from a nitrogen source).

At the beginning of culture, the cells were cultured under aerobic conditions at a stirring rate of 200 rpm. At the 48th hour, the aerobic conditions were changed to microaerobic conditions at a stirring rate of 50 rpm. After sampling the culture medium, the flask was again closed with Silicosen, and culture with shaking at 33° C. was continued for batch culture. FIGS. 15 and 16 show the results.

As shown in the results of FIGS. 15 and 16, it is difficult to add 15 g/L or more of sodium nitrate, because of the relationship with the salt concentration. In the case of urea, the nitrogen equivalent is doubled; therefore, cells can be grown at a lower concentration than sodium nitrate. Further, when the culture conditions were changed to microaerobic conditions at the 48th hour, the degradation of PHB and the secretion of 3-hydroxybutyric acid readily occurred. This revealed that urea could be effectively used as the nitrogen source.

The invention claimed is:

1. A process for producing 3-hydroxybutyric acid or a salt thereof, the process comprising the following steps (a) to (d):
   (a) culturing one or more halophilic bacteria belonging to the genus *Halomonas* under aerobic conditions in a medium containing an organic carbon source and an inorganic salt to produce poly-3-hydroxybutyrate (PHB);
   (b) changing the culture conditions in step (a) from aerobic culture to microaerobic culture by reducing the oxygen concentration;
   (c) adjusting the pH of the culture medium at 7.5 or more if the pH is less than 7.5 after step (b), causing the bacterial cells to produce 3-hydroxybutyric acid or a salt thereof in the culture medium, and maintaining the pH of the culture medium at 7.5or more after the 3-hydroxybutyric acid or a salt thereof begins to form; and
   (d) collecting the 3-hydroxybutyric acid or the salt thereof from the culture medium obtained in step (c).

2. The production process according to claim 1, wherein the culture conditions are changed from aerobic culture to microaerobic culture in step (b) when the amount of PHB accumulated in the bacterial cells is 70 parts by weight of PHB or more per 100 parts by weight of dry cells.

3. The production process according to claim 1, wherein before step (b), the process comprises a step of adding at least one member selected from the group consisting of a nitrogen source, a metal salt, and borate to the culture medium.

4. The production process according to claim 3, wherein, before step (b), the process comprises a step of adding a nitrogen source to the culture medium, and the nitrogen source is at least one member selected from the group consisting of nitrate, nitrite, ammonium salts, and urea.

5. The production process according to claim 3, wherein, before step (b), the process comprises a step of adding a metal salt to the culture medium, and the metal salt is at least one member selected from the group consisting of zinc salts, molybdenum salts, manganese salts, copper salts, and cobalt salts.

6. The production process according to claim 3, wherein at least one member selected from the group consisting of a nitrogen source, a metal salt, and borate is added to the culture medium when the amount of PHB accumulated in the bacterial cells is 70 parts by weight of PHB or more per 100 parts by weight of dry cells.

7. The production process according to claim 1, wherein before step (b), the process comprises a step of reducing the volume of the culture medium.

8. The production process according to claim 1, wherein the pH of the culture medium is adjusted and maintained in step (c) using at least one member selected from the group consisting of hydroxide, carbonate, and hydrogen carbonate.

9. The production process according to claim 1, wherein the halophilic bacteria comprise *Halomonas* sp. KM-1 strain (FERM BP-10995).

10. The production process according to claim 2, wherein before step (b), the process comprises a step of adding at least one member selected from the group consisting of a nitrogen source, a metal salt, and borate to the culture medium.

11. The production process according to claim 10, wherein, before step (b), the process comprises a step of adding a nitrogen source to the culture medium, and the nitrogen source is at least one member selected from the group consisting of nitrate, nitrite, ammonium salts, and urea.

12. The production process according to claim 11, wherein, before step (b), the process comprises a step of adding a metal salt to the culture medium, and the metal salt is at least one member selected from the group consisting of zinc salts, molybdenum salts, manganese salts, copper salts, and cobalt salts.

13. The production process according to claim 12, wherein the metal salt is added to the culture medium when the amount of PHB accumulated in the bacterial cells is 70 parts by weight of PHB or more per 100 parts by weight of dry cells.

14. The production process according to claim 13, wherein before step (b), the process comprises a step of reducing the volume of the culture medium.

15. The production process according to claim 14, wherein the pH of the culture medium is adjusted and maintained at 8 or more in step (c).

16. The production process according to claim 11, wherein the nitrogen source is added to the culture medium when the amount of PHB accumulated in the bacterial cells is 70 parts by weight of PHB or more per 100 parts by weight of dry cells.

17. The production process according to claim 16, wherein before step (b), the process comprises a step of reducing the volume of the culture medium.

18. The production process according to claim 17, wherein the pH of the culture medium is adjusted and maintained at 8 or more in step (c).

19. The production process according to claim 1, wherein the pH of the culture medium is adjusted and maintained at 8 or more in step (c).

20. The production process according to claim 19, wherein the pH of the culture medium is adjusted and maintained at 8.5 or more in step (c).

21. The production process according to claim 1, wherein the pH of the culture medium in step (a) is 8.8 to 12.

* * * * *